(12) United States Patent
Ramsey et al.

(10) Patent No.: US 9,006,648 B2
(45) Date of Patent: Apr. 14, 2015

(54) MICROCHIPS WITH INTEGRATED MULTIPLE ELECTROSPRAY IONIZATION EMITTERS AND RELATED METHODS, SYSTEMS AND DEVICES

(75) Inventors: John Michael Ramsey, Chapel Hill, NC (US); Andrew Chambers, Wildwood, MO (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/001,549

(22) PCT Filed: Mar. 5, 2012

(86) PCT No.: PCT/US2012/027662
§ 371 (c)(1),
(2), (4) Date: Aug. 26, 2013

(87) PCT Pub. No.: WO2012/125318
PCT Pub. Date: Sep. 20, 2012

(65) Prior Publication Data
US 2013/0327936 A1    Dec. 12, 2013

Related U.S. Application Data

(60) Provisional application No. 61/451,667, filed on Mar. 11, 2011.

(51) Int. Cl.
*H01J 49/04*      (2006.01)
*H01J 49/16*      (2006.01)
*H01J 49/10*      (2006.01)
*B05B 5/025*      (2006.01)

(52) U.S. Cl.
CPC ............. *H01J 49/107* (2013.01); *H01J 49/165* (2013.01); *B05B 5/025* (2013.01)
USPC .......................................... 250/288; 250/282

(58) Field of Classification Search
CPC ... H01J 49/04; H01J 49/0409; H01J 49/0431; H01J 49/0445; H01J 49/165; H01J 49/167
USPC .......................................... 250/281, 282, 288
See application file for complete search history.

(56) References Cited

U.S. PATENT DOCUMENTS

| | | | |
|---|---|---|---|
| 5,872,010 A * | 2/1999 | Karger et al. | 436/173 |
| 6,110,343 A | 8/2000 | Ramsey et al. | |
| 6,231,737 B1 | 5/2001 | Ramsey et al. | |
| 6,690,006 B2 | 2/2004 | Valaskovic | |

(Continued)

OTHER PUBLICATIONS

Dayon et al, "Multitrack Electrospray Chips", Journal of Mass Spectrometry, 2006; 41, 1484-1490.*

(Continued)

*Primary Examiner* — Nicole Ippolito
*Assistant Examiner* — David E Smith
(74) *Attorney, Agent, or Firm* — Myers Bigel Sibley & Sajovec, P.A.

(57) ABSTRACT

Microchips which are particularly suitable for use with a mass spectrometer include a microchip body with at least one fluid channel formed into the microchip body and at least two flat monolithic closely spaced integrated ESI (electrospray ionization) emitters defined by shaped projections formed to extend from one side of the microchip body, a respective one being in fluid communication with a fluid channel. Related systems and methods are also described.

24 Claims, 17 Drawing Sheets

(56) References Cited

U.S. PATENT DOCUMENTS

| | | | |
|---|---|---|---|
| 6,803,568 | B2* | 10/2004 | Bousse et al. ............ 250/288 |
| 2002/0000516 | A1 | 1/2002 | Schultz et al. |
| 2002/0117629 | A1 | 8/2002 | Fujimaki et al. |
| 2002/0190204 | A1* | 12/2002 | Hofstadler et al. ......... 250/288 |
| 2003/0146377 | A1 | 8/2003 | Miller et al. |
| 2003/0224531 | A1 | 12/2003 | Brennen et al. |
| 2004/0166504 | A1* | 8/2004 | Rossier et al. ............... 435/6 |
| 2007/0057179 | A1* | 3/2007 | Bousse et al. .............. 250/288 |
| 2007/0145263 | A1* | 6/2007 | Weng ........................ 250/288 |
| 2010/0075428 | A1* | 3/2010 | Wang et al. ................. 436/86 |

OTHER PUBLICATIONS

International Search Report for corresponding PCT Application No. PCT/US2012/027662, Date of Mailing Sep. 25, 2012.

Chambers et al. "Monolithic Integration of Two-Dimensional Liquid Chromatography-Capillary electrophoresis and Electrospray Ionization on a Microfluidic Device", *Analytical Chemistry*, 2011, 83:842-849.

Charles L. "Flow injection of the lock mass standard for accurate mass measurement in electrospray ionization time-of-flight mass spectrometry coupled with liquid chromatography", *Rapid Communications in Mass Spectrometry*, 2003, 17:1383-1388.

Dayon et al. "Multitrack electrospray chips", *Journal of Mass Spectrometry*, 2006, 41:1484-1490.

Flora et al. "High-Mass Accuracy of Product Ions Produced by SORI-CID Using a Dual Electrospray Ionization Source Coupled with FTICR Mass Spectrometry", *Anal. Chem.*, 2001, 73:1247-1251.

Hardenborg et al. "Novel polyamine coating providing non-covalent deactivation and reversed electroosmotic flow of fused-silica capillaries for capillary electrophoresis", *Journal of Chromatography A.*, 1003 (2003), 217-221.

Jiang et al. "Development of Multi-ESI-Sprayer, Multi-Atmospheric-Pressure-inlet Mass Spectrometry and its Application to Accurate Mass Measurement Using Time-of-Flight Mass Spectrometry", *Anal. Chem.*, 2000, 72, 20-24.

Kelly et al. "Array of Chemically Etched Fused-Silica Emitters for Improving the Sensitivity and Quantitation of Electrospray Ionization Mass Spectrometry", *Anal. Chem.*, 2007, 79:4192-4198.

Mellors et al. "A Microfabricated Device for Performing Comprehensive Online LC-CE-MS for Proteomics Applications", *Twelfth International Conference on Miniaturized Systems for Chemistry and Life Sciences*, Oct. 12-16, 2008, San Diego, California, USA, 1937-1939.

Mellors et al. "Fully Integrated Glass Microfluidic Device for Performing High-Efficiency Capillary Electrophoresis and Electrospray Ionization Mass Spectrometry", *Anal.Chem.* 2008, 80:6881-6887.

Prudent et al. "Microfabricated Dual Sprayer for On-Line Mass Tagging of Phosphopeptides", *Anal. Chem.* 2008, 80:2531-2538.

Rulison et al. "Scaleup of electrospray atomization using linear arrays of Taylor cones", *Review of Scientific Instruments*, 64, 683-686, (1993).

Satomi et al. "Accurate mass measurement in nano-electrospray ionization mass spectrometry by alternate switching of high voltage between sample and reference sprayers", *Rapid Communications in Mass Spectrometry*, 2005, 19:540-546.

Schneider et al. "Multiple sprayer system for high-throughput electrospray ionization mass spectrometry", *Rapid Communications in Mass Spectrometry*, 2002, 16:1982-1990.

Zhou et al. "High accuracy mass measurement of peptides with internal calibration using a dual electrospray ionization sprayer system for protein identification", *Rapid Communications in Mass Spectrometry*, 2002, 16:505-511.

Extended European Search Report for corresponding EP Application No. EP12757244.4, Feb. 12, 2015, 12 pages.

* cited by examiner

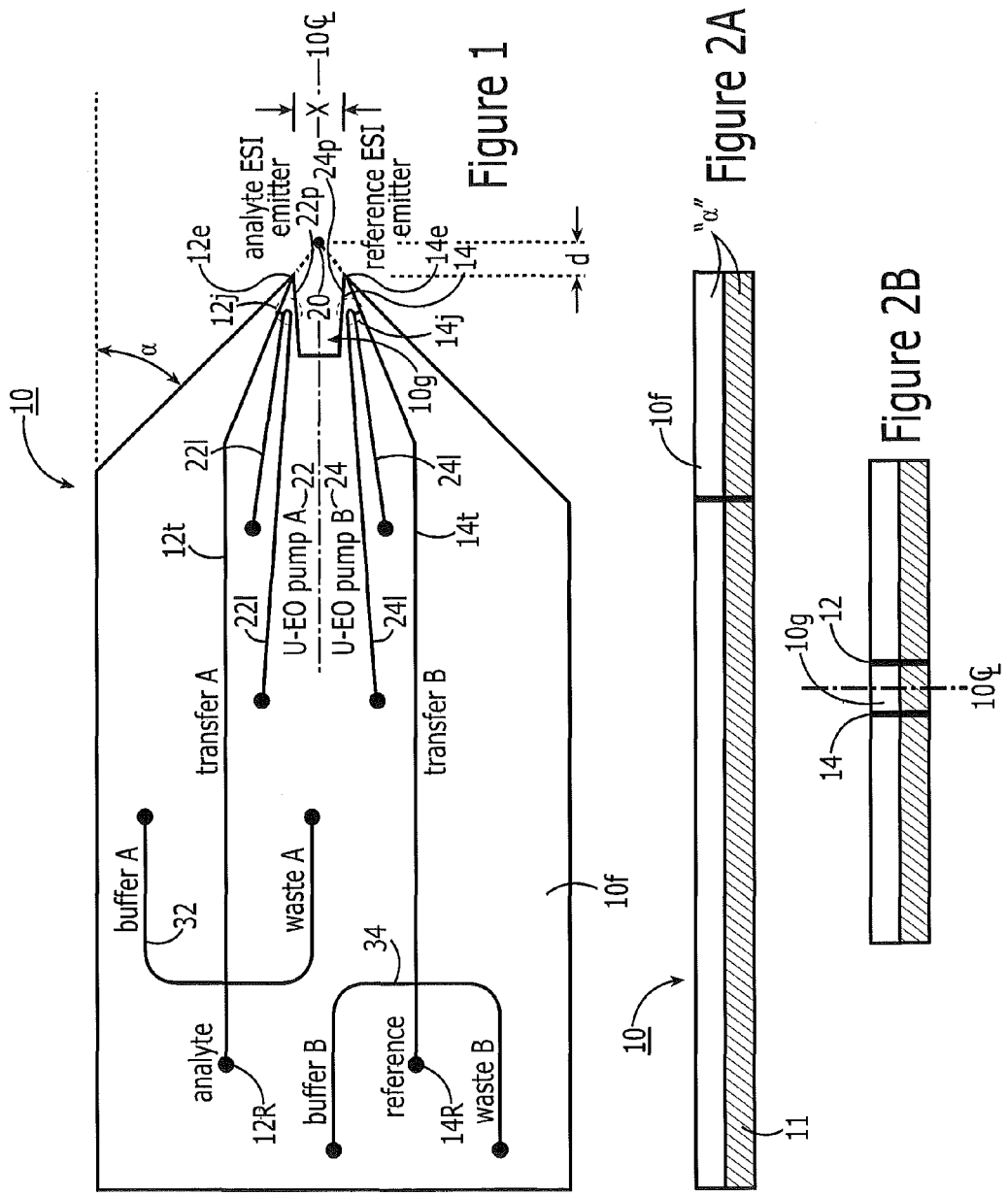

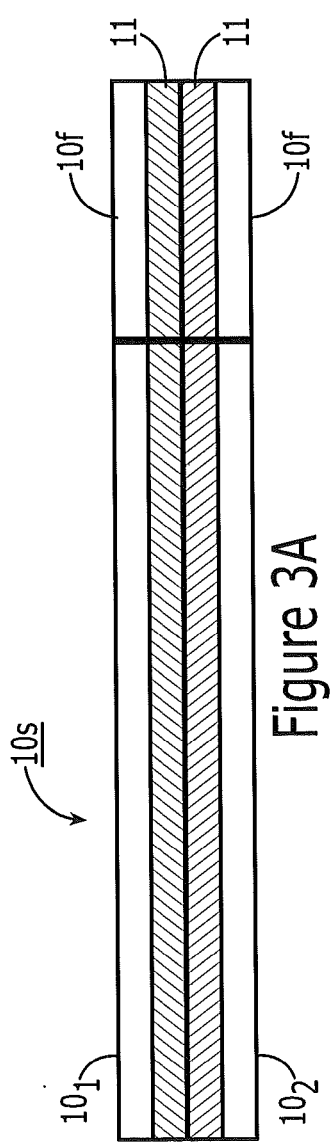
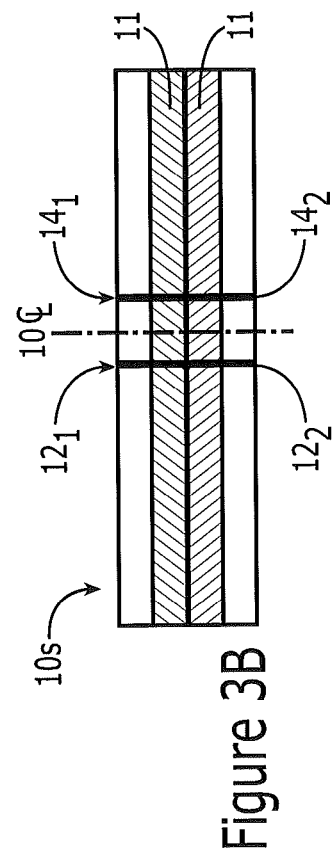
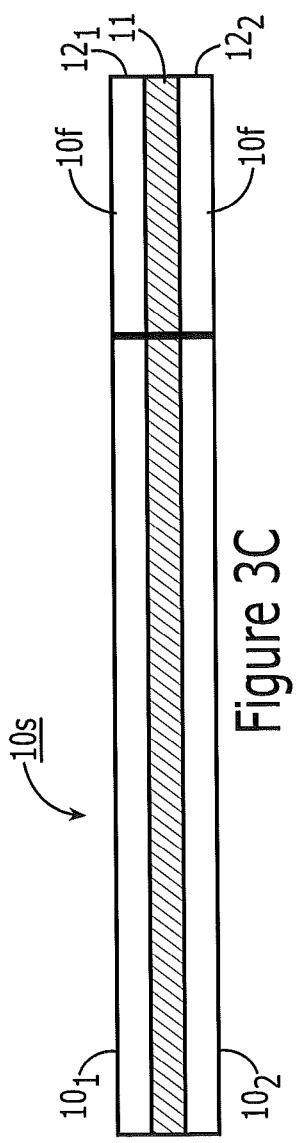
Figure 3A
Figure 3B
Figure 3C

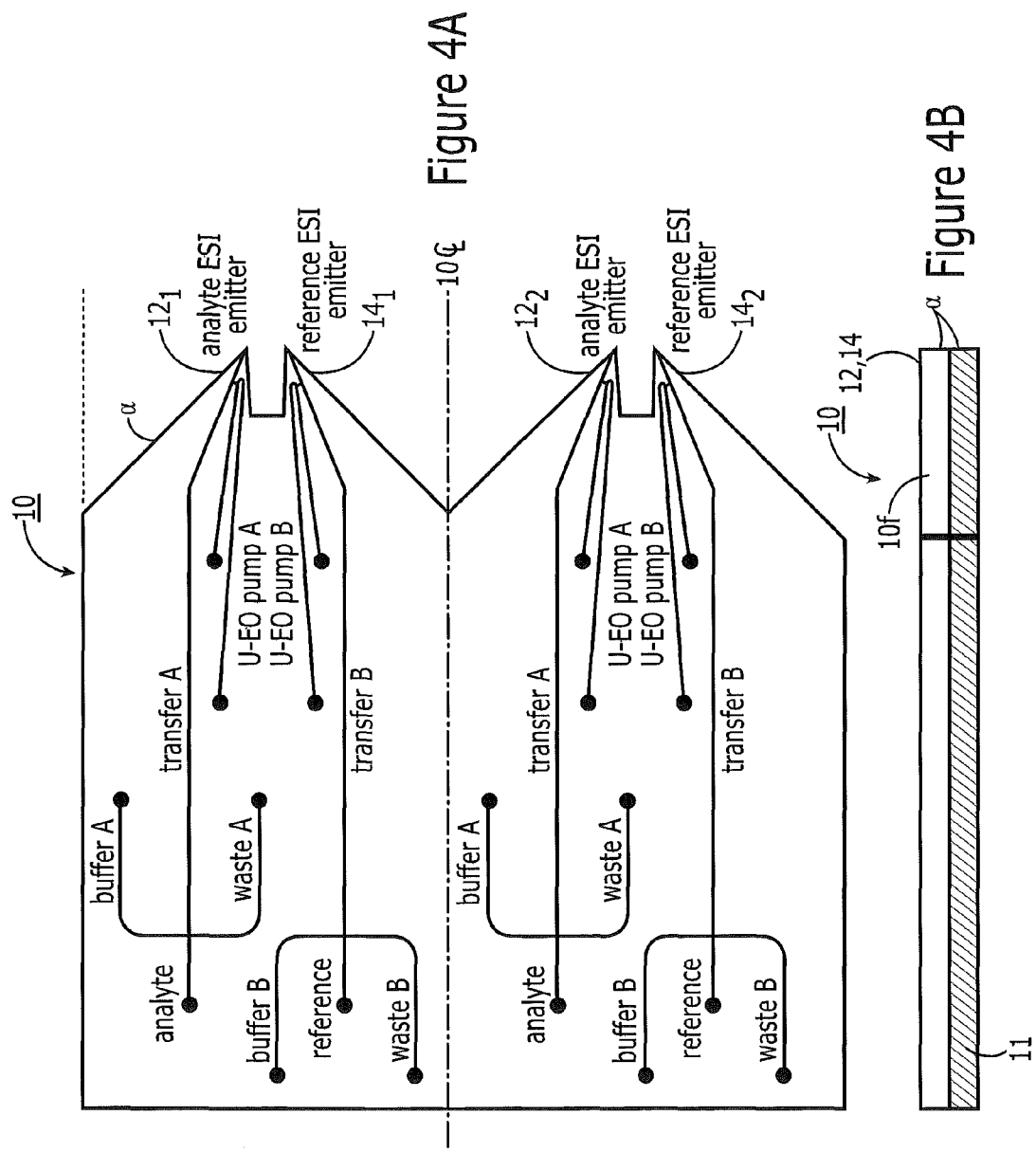

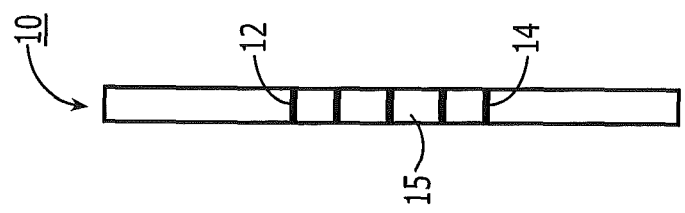
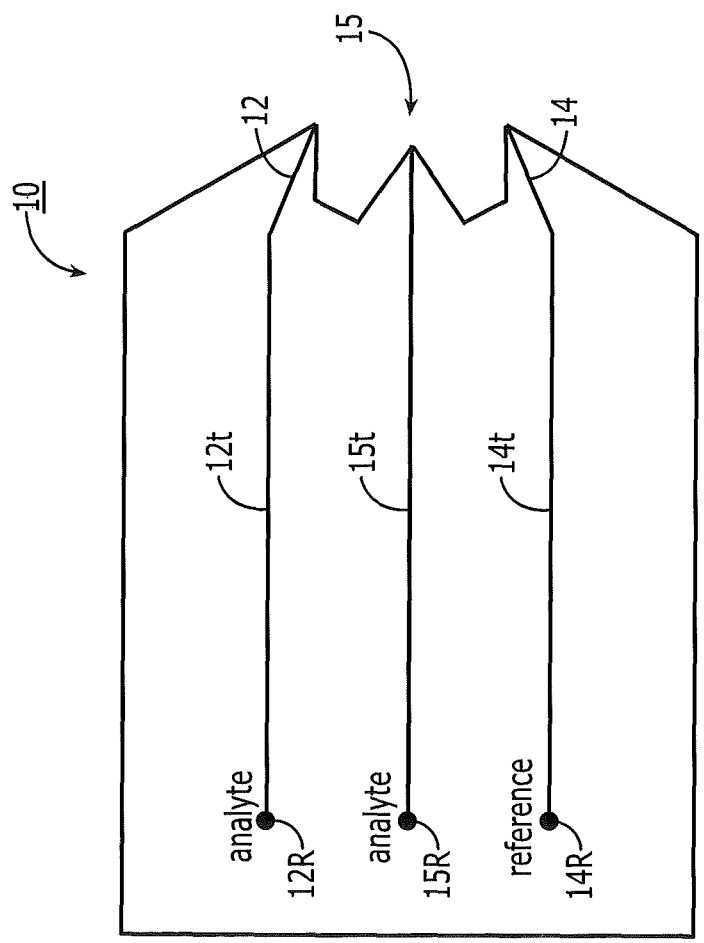
Figure 5B
Figure 5A

Microchip dual ESI device with analyte emitter active.

Microchip dual ESI device with reference emitter active.

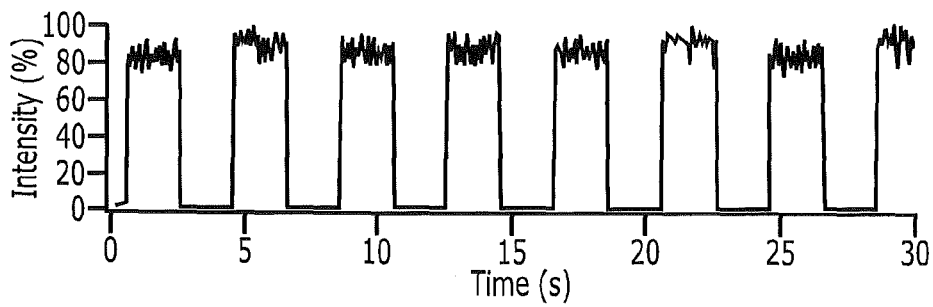

Sequential sampling of analyte and reference materials every 2 s. Reconstructed ion chromatograms are shown for reference signal [reserpine].

Figure 17A

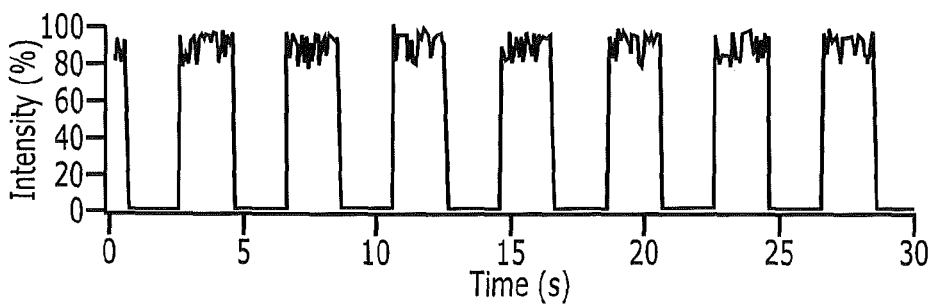

Sequential sampling of analyte and reference materials every 2 s. Reconstructed ion chromatograms are shown for analyte signal [leucine enkephalin].

Figure 17B

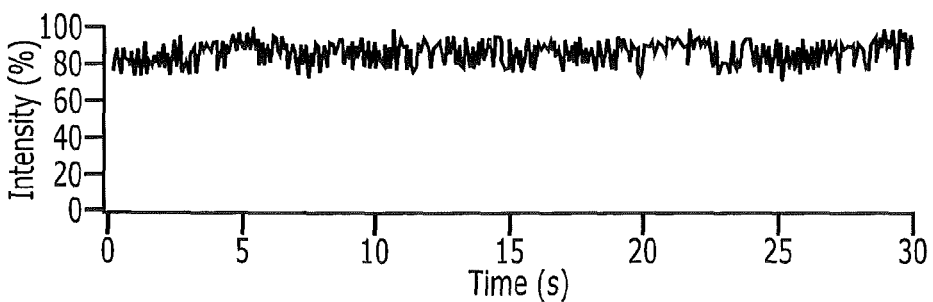

Sequential sampling of analyte and reference materials every 2 s. Reconstructed ion chromatograms are shown for the combined reference and analyte signal.

Figure 17C

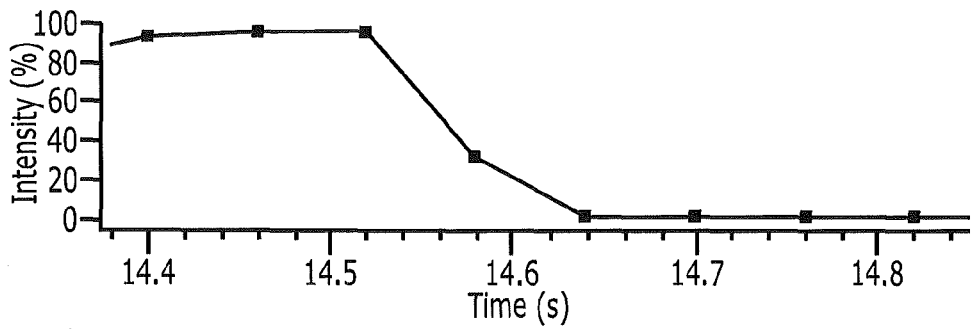

Enlarged section of the data in Figure 17. Reconstructed ion chromatogram shown for reference signal [reserpine]. At 14.52 s the reference electrospray is turned off and the analyte electrospray is turned on.

Figure 18A

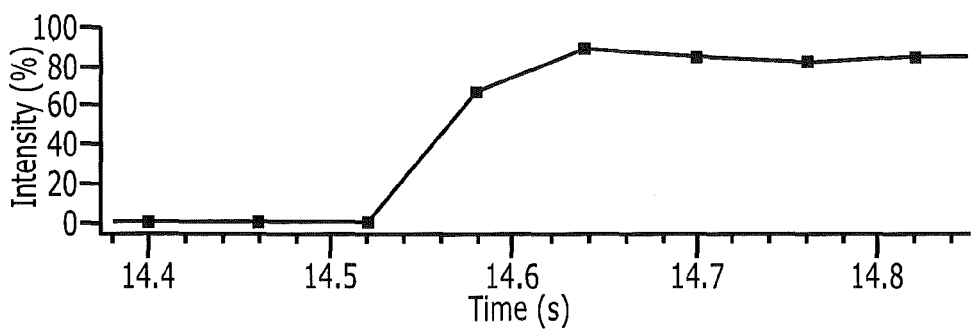

Enlarged section of the data in Figure 17. Reconstructed ion chromatogram shown for analyte signal [leucine enkephalin]. At 14.52 s the reference electrospray is turned off and the analyte is turned on.

Figure 18B

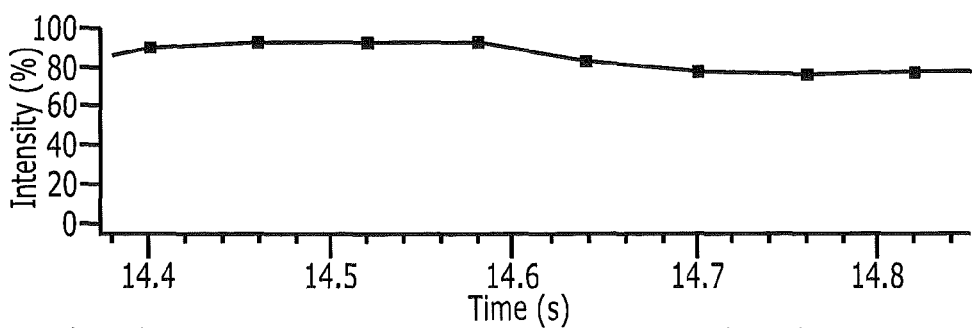

Enlarged section of the data in Figure 17. Reconstructed ion chromatogram shown for the combined reference and analyte signal. At 14.52 s the reference electrospray is turned off and the analyte electrospray is turned on.

Figure 18C

One minute of summed mass spectra from the reference [reserpine] data file.

One minute of summed mass spectra from the analyte [leucine enkephalin] data file.

The mass measurement errors for infusion ESI-MS of leucine enkephalin.
Raw data (open circles), corrected data (closed circles).

MICROCHIPS WITH INTEGRATED MULTIPLE ELECTROSPRAY IONIZATION EMITTERS AND RELATED METHODS, SYSTEMS AND DEVICES

STATEMENT OF FEDERAL SUPPORT

This invention was made with government support under by Grant No. N66001-09-1-2055 from the Department of Defense. The United States government has certain rights in the invention.

RELATED APPLICATIONS

This application is a 35 USC §371 national phase application of PCT/US2012/027662, International Filing Date Mar. 5, 2012, which claims the benefit of and priority to U.S. Provisional Application Ser. No. 61/451,667, filed Mar. 11, 2011, the content of which is hereby incorporated by reference as if recited in full herein.

FIELD OF THE INVENTION

This invention relates to devices that interface with mass spectrometers for rapid mass measurements.

BACKGROUND OF THE INVENTION

Electrospray ionization ("ESI") is an important technique for the analysis of biological materials contained in solution by mass spectrometry. See, e.g., Cole, R. B. *Electrospray Ionization Mass Spectrometry: Fundamentals, Instrumentation & Applications*; John Wiley and Sons, Inc.: New York, 1997. Electrospray ionization was developed in the late 1980s and was popularized by the work of Fenn. See, e.g., Fenn J B, Mann M, Meng C K, Wong S F & Whitehouse C M (1989) ELECTROSPRAY IONIZATION FOR MASS-SPECTROMETRY OF LARGE BIOMOLECULES. *Science* 246, 64-71. Simplistically, electrospray ionization involves the use of electric fields to disperse a sample solution into charge droplets. Through subsequent evaporation of the droplets, analyte ions contained in the droplet are either field emitted from the droplet surface or the ions are desolvated resulting in gas phase analyte ions. The source of the liquid exposed to the electric field and to be dispersed is ideally one of small areal extent as the size of the electrospray emitter directly influences the size of droplets produced. Smaller droplets desolvate more rapidly and have fewer molecules present per droplet leading to greater ionization efficiencies. These ions can be characterized by a mass analyzer to determine the mass-to-charge ratio. Further analyte structural information can be obtained by employing tandem mass spectrometry techniques.

The chemical informing power of electrospray ionization—mass spectrometry can be enhanced when the electrospray emitter is coupled to liquid-phase chemical separations such as liquid chromatography, capillary electrophoresis, or ion exchange chromatography, to name a few. These chemical separation techniques endeavor to deliver isolated compounds to the electrospray emitter to reduce ionization suppression and mass spectral complexity. More recently, chemical separation systems have been implemented on microfabricated fluidic devices that also have attempted to incorporate integrated electrospray emitters. See, e.g., Xue Q, Foret F, Dunayevskiy Y M, Zavracky P M, McGruer N E & Karger B L (1997), Multichannel Microchip Electrospray Mass Spectrometry. *Anal Chem* 69, 426-430, Ramsey R S & Ramsey J M (1997), Generating Electrospray from Microchip Devices Using Electroosmotic Pumping. *Anal Chem* 69, 1174-1178, Chambers A G, Mellors J S, Henley W H & Ramsey J M (2011), Monolithic Integration of Two-Dimensional Liquid Chromatography—Capillary Electrophoresis and Electrospray Ionization on a Microfluidic Device. *Analytical Chemistry* 83, 842-849.

Despite the foregoing, there remains a need for alternate microfluidic devices with ESI emitters that can be operated on a rapid time scale, increase ionization efficiency, and increase ion flux to enhance the performance of electrospray ionization—mass spectrometry analysis of chemical and biochemical materials.

SUMMARY OF EMBODIMENTS OF THE INVENTION

Embodiments of the invention are directed to planar microfluidic devices (microchips) with monolithically integrated ESI emitters that are fabricated directly onto the microchip to facilitate near zero dead-volume integration with microscale separations.

Embodiments of the invention are directed to mass spectrometer analyzer systems. The systems include a mass spectrometer with an inlet orifice and a flat microchip comprising a perimeter with four sides and at least a first and second monolithic ESI emitter. The first and second ESI emitters reside on one side of the microchip and, during operation, are aligned proximate the mass spectrometer inlet orifice. The system also includes a control circuit configured to control fluid flow in the microchip to substantially synchronize emitter spray with data acquisition of the mass spectrometer.

The system can include at least one power supply in communication with the microchip. The control circuit is in communication with the power supply and is configured to direct the at least one power supply to deliver power to the microchip to controllably cause the at least one ESI emitter to spray.

The control circuit can be configured to sequentially power the first and second ESI emitters.

The first ESI emitter can be an analyte spray emitter and the second ESI emitter can be a reference spray emitter. The system can be configured to adjust analyte data associated with the ESI analyte emitter collected by the mass spectrometer using reference data associated with the ESI reference emitter collected by the mass spectrometer to provide corrected analyte data measurements.

The first and second ESI emitters can be in communication with a respective EO pump channel held by the microchip. The at least one power supply includes a first power supply in communication with the first ESI emitter and a second power supply in communication with the second ESI emitter. The control circuit can be configured to sequentially operate the first and second power supplies and synchronize the mass spectrometer data acquisition of emitter spray with switching of the first and second power supplies.

In some embodiments, the mass spectrometer has an onboard mechanical baffle output circuit with a trigger voltage and the control circuit is configured to switch the first and second power supplies on and off using the trigger voltage.

The microchip can be rigid and have ESI emitters positioned proximate a corner of the microchip.

The microchip can be rigid and have ESI emitters positioned spaced inwardly from corners and apart from each other.

The microchip can be rigid and have a plurality of stacked ESI emitters.

The microchip can be rigid and the at least first and second ESI emitters can be provided as a series of between about 2-100 closely spaced emitters residing on one corner of the microchip.

Other embodiments are directed to methods of obtaining sample data. The methods include: (a) providing a microchip with EO pump channels and monolithic integrated separate reference and analyte ESI emitters residing on a first end of the microchip; (b) activating at least one emitter by supplying voltage to a corresponding EO pump channel; and (c) acquiring signal data from spray plumes emitted by the respective separate emitters using a mass spectrometer positioned proximate the microchip.

The method can also include electronically adjusting analyte data using the reference data.

The activating step can be carried out by selectively activating one emitter at a time by supplying a high voltage to a corresponding EO pump channel. The acquiring data step can be carried out by obtaining reference data before and/or after obtaining calibration data.

The method can include electronically synchronizing the mass spectrometer data acquisition with the activating step. Optionally, the electronically synchronizing step is carried out using an electrical component onboard the mass spectrometer. The onboard component can include, for example, a baffle control circuit having a trigger voltage output used to switch power supplies used to apply the voltage to the microchip EO pump channels.

The integrated separate ESI emitters can be dual emitters residing closely spaced apart about a single corner of the microchip or about a centerline of the microchip.

The integrated separate ESI emitters can include stacked emitters.

The stacked emitters can reside closely spaced apart about a single corner of the microchip.

The emitters can be provided as between about 2-100 emitters closely spaced apart about a single corner of the microchip.

The reference emitter can be provided as a set of emitters that concurrently spray reference spray plumes in response to the activating step, and the analyte emitter can be provided as a set of emitters that concurrently spray analyte spray plumes in response to the activating step.

Yet other embodiments are directed to a microchip for use with a mass spectrometer. The microchip includes a substantially rigid and planar microchip body, at least one fluid channel formed into the microchip body, and at least two flat closely spaced integrated ESI (electrospray ionization) emitters defined by shaped projections formed to extend from one side of the microchip body in fluid communication with at least one of the at least one fluid channel.

The microchip can include at least two EO (electroosmotic) pump channels, one for each of the ESI emitters.

The at least two emitters can reside between about 0.1-6 mm apart about one side of the microchip with a gap space therebetween.

The at least two emitters can be provided as between about 4-100 closely spaced emitters positioned on one corner of the microchip.

The emitters are defined by sharp monolithic tips formed in the microchip body.

The at least two emitters can be positioned about one corner of the microchip.

The microchip can include a first nanojunction that connects a first reference transfer channel with a corresponding U or V-shaped EO pump channel and a second nanojunction that connects a second analyte channel with a corresponding U or V-shaped EO pump channel.

The microchip body can have a perimeter shape with first and second parallel long sides and a third straight side connecting one end of the first and second long sides, and a fourth side with first and second segments that angle inward from the first and second long sides to respective emitters having sharp tips and being spaced apart by a gap space in the microchip body.

The at least two ESI emitters can be a series of closely spaced sharp tips residing about one corner of the microchip, all in fluid communication with the same fluid channel.

The at least two ESI emitters can include at least two emitters that reside in parallel layers, one above another.

At least two of the at least two ESI emitters can be stacked at a common position on a corner of the microchip body.

The microchip body can have at least four stacked ESI emitters, two ESI emitters being co-planar and on a first layer and another two being co-planar and on a second layer.

Still other embodiments are directed to methods of forming a fluid microchip with ESI emitters for use with a mass spectrometer. The methods include: (a) providing a first substantially rigid substrate; (b) forming fluid flow channels thereon; (c) attaching a second substrate to the first substrate to enclose the fluid flow channels therebetween; then (d) forming projections on a first end of the attached first and second substrates to define at least two ESI (electrospray ionization) emitters.

The forming projections step can be carried out by cutting sharp tips into the first and second substrates.

The method can also include forming EO (electroosmotic) pump channels and nanojunctions to connect a first fluid channel to a first EO pump channel and a second fluid channel to a second EO pump channel, the nanojunctions residing proximate a respective ESI emitter.

The forming the projections step can be carried out to form at least two spaced apart tips with flat upper and lower surfaces that reside spaced apart from corners of the substrates.

The forming the projections step can be carried out by cutting the attached substrates in a defined pattern.

The method can include, before the forming projections step: (i) forming fluid flow channels on a third substrate; (ii) attaching the third substrate to the second substrate or to a fourth substrate to enclose the fluid flow channels therebetween; (iii) and attaching the substrates to define a microchip body. The forming projections step is carried out by forming the projections on a first end of the attached first, second, third and, where used fourth, substrates to define at least two stacked ESI (electrospray ionization) emitters.

Embodiments of the invention are directed to microchips with a substantially rigid and planar microchip body, at least one elongate fluid channel formed into the microchip body, at least two closely spaced integrated ESI (electrospray ionization) emitters defined by shaped projections formed to extend from at least one side of the microchip body, a respective one being in fluid communication with one of the fluid channels. In some particular embodiments, the microchip can include at least two EO (electroosmotic) pump channels, one for each of the ESI emitters. The at least two emitters can reside between about 0.1-6 mm apart about a medial or corner portion of the one side of the microchip. The emitters can be defined by sharp tips formed in the microchip body.

The at least one channels can be at least two elongate fluid channels, including a first reference transfer channel and a second analyte transfer channel that extend to the emitters tips. The microchips can include a first nanojunction that connects the first reference transfer channel with a corresponding U-shaped EO pump channel and a second nanojunction that connects the second analyte channel with a corresponding U-shaped EO pump channel.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIG. 1 is a schematic illustration of an exemplary microchip with dual ESI emitters according to embodiments of the present invention.

FIG. 2A is a (long) side view and FIG. 2B is an end view (e.g., short side) of the microchip shown in FIG. 1 according to embodiments of the present invention.

FIG. 3A is a (long) side view of another embodiment of a microchip according to embodiments of the present invention.

FIG. 3B is an end view of the device of FIG. 3A according to embodiments of the present invention.

FIG. 3C is a long side view of a multilayer microchip similar to that shown in FIG. 3A but with three stacked substrates (rather than four) to form stacked parallel emitters according to embodiments of the present invention.

FIG. 4A is a schematic top view of yet another exemplary microchip according to embodiments of the present invention.

FIG. 4B is an end view of the device shown in FIG. 4A according to embodiments of the present invention.

FIG. 5A is a top view of yet another embodiment of a microchip according to embodiments of the present invention.

FIG. 5B is a side view of the microchip shown in FIG. 5A according to embodiments of the present invention.

FIGS. 17A-17C are graphs of intensity (percentage) over time (seconds) for reconstructed ion chromatograms based on sequential sampling of analyte and reference materials every 2 seconds. FIG. 17A shows the reference signal (reserpine). FIG. 17B shows the analyte signal (leucine enkephalin). FIG. 17C shows the combined reference and analyte signal.

FIGS. 18A-18C are graphs of intensity (percentage) versus time (seconds) enlarging a time segment (between about 14.4 seconds to 14.8 seconds) of data shown in FIGS. 17A-17C. At 14.52 seconds, the reference electrospray is turned off and the analyte spray is turned on.

FIG. 19A shows the reference data file and FIG. 19B shows the analyte data file.

DESCRIPTION OF EMBODIMENTS OF THE INVENTION

Figure 6A:
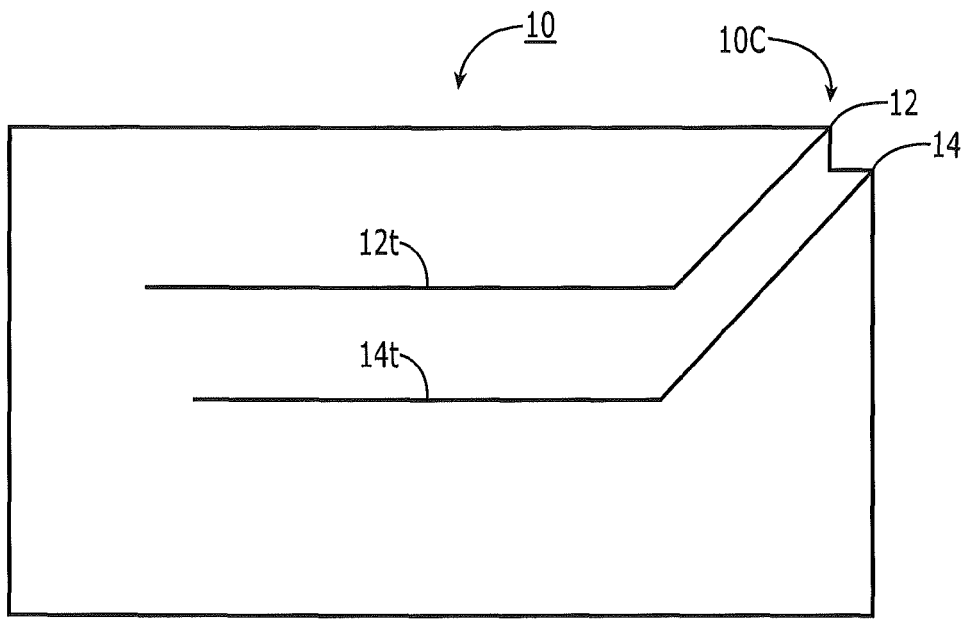
FIG. 6A is a top view of another embodiment of a microchip according to some embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. Well-known functions or constructions may not be described in detail for brevity and/or clarity.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The term "microchip" refers to a substantially planar, thin, and, in some embodiments, rigid device. The term "thin" refers to a thickness dimension that is less than about 5 mm. The microchip typically has a width and length that is less than about 6 inches and a thickness that is less than about 5 mm, typically between about 2000 $\mu$m to about 250 $\mu$m. The terms "integrated" and "integral" and derivatives thereof, when referring to ESI emitters, mean that the respective emitters are formed directly into and/or by a substrate(s). The term "high voltage" refers to voltage in the kV range, typically between about 2-10 kV. The term "microfluidic" refers to fluid flow channels that have sub-millimeter or smaller size width and/or depth (e.g., the term includes nanometer size channels) and includes channels with width or depth in a size range of about tens to hundreds of microns.

The term "analyte" refers to a substance undergoing analysis, typically a substance having an ion or ions of interest in a m/z range of interest, that can be evaluated using microchip emitters. The term "reference" with respect to a fluid, solution, material or analyte refers to a substance having known properties that can be optionally electrosprayed using one or more of the onboard emitters. The reference and analyte material can both be fluids and may be the same fluids or may be different fluids. The reference and analyte materials can comprise biomolecules such as polymers, peptides, proteins and the like. For example, an analyte can comprise leucine enkephalin and a reference can comprise reserpine. The microchips can be configured to hold any collection of samples possible to spray out of multiple emitters, i.e., from N=2 to N=1000 or even more different samples from respective emitters. The different samples can be of the same sample type or material or of a different sample type of material. The microchips do not require a reference analyte or reference fluid to be emitted or used.

All of the document references (patents, patent applications and articles) are hereby incorporated by reference as if recited in full herein.

Embodiments of the invention provide a system 50 (FIG. 12A, 12B) with a mass spectrometer 75 and microchips 10 that cooperate with a mass spectrometer 75 that allow an analyte to be sprayed from one or more emitters. In some embodiments, the microchip 10 can be configured to spray both an analyte and a reference material from respective ESI emitters. However, the microchips 10 can be used with other analysis methods and systems including spraying onto a plate or other surface for another evaluation.

In particular embodiments, the analyte and reference materials are sequentially sprayed to avoid interference that can arise if both have the same nominal mass to charge (m/z) value or ionization suppression effects, one on the other.

In some embodiments, the microchips 10 can be used for deposition onto a substrate for subsequent analysis. For example, the microchips 10 can spray or emit fluid from one or more ESI emitters onto a planar substrate for subsequent analysis by Matrix-assisted laser desorption/ionization (MALDI). See, e.g., Morozov V N (2010) Electrospray Deposition of Biomolecules. In *Nano/Micro Biotechnology*, pp. 115-162 and Hensel R R, King R C & Owens K G (1997) Electrospray sample preparation for improved quantitation in matrix-assisted laser desorption/ionization time-of-flight mass spectrometry. *Rapid Communications in Mass Spectrometry* 11, 1785-1793. MALDI is one of the two "soft" ionization techniques besides electrospray ionization (ESI) that allow for the sensitive detection of large, non-volatile and labile molecules by mass spectrometry. MALDI has developed into an indispensable tool in analytical chemistry, and in analytical biochemistry in particular.

Embodiments of the invention provide microchips 10 that can accommodate several processes for chemical analysis (e.g., sample clean-up, pre-concentration, and separation) that can be integrated on the same microfabricated device with near-zero dead volume connections. The microchips 10 can also be used alone and/or configured for electrospray without any separation or processing elements. Where used, the integration may allow for rapid processing of small sample quantities while reducing the overall complexity of the instrumentation. The scale of microfluidic separations matches well with the ESI-MS process, which has been shown to be more sensitive at low flow rates. See, e.g., Wilm, M. S.; Mann, M. Electrospray and Taylor-Cone Theory, Doles Beam of Macromolecules at Last. *Int. J. Mass Spectrom. Ion Processes* 1994, 136, 167; Wilm, M.; Mann, M. Analytical properties of the nanoelectrospray ion source. *Anal. Chem.* 1996, 68, 1; Emmett, M. R.; Caprioli, R. M. Micro-Electrospray Mass-Spectrometry—Ultra-High-Sensitivity Analysis of Peptides and Proteins. *J. Am. Soc. Mass Spectrom.* 1994, 5, 605; and Valaskovic, G. A.; Kelleher, N. L.; Little, D. P.; Aaserud, D. J.; McLafferty, F. W. Attomole-Sensitivity Electrospray Source for Large-Molecule Mass-Spectrometry. *Anal. Chem.* 1995, 67, 3802.

FIG. 1 is a schematic illustration of an exemplary microchip 10 with at least two (shown as dual) ESI emitters 12, 14. As shown, the emitters 12, 14 can be substantially planar and reside closely spaced apart on a single side (inward from corners thereof) of the microchip 10. As shown, the microchip 10 can be configured as a planar microfluidic device. The microchip 10 can have one, two or more reservoirs in fluid communication with a respective channel. As shown, the microchip 10 has at least one analyte reservoir 12r and at least one other reservoir 14r which may be a reference reservoir or another analyte reservoir and associated transfer channels 12t, 14t that extend to the corresponding ESI emitter 12, 14. The analyte reservoir 12r holds a sample to be analyzed and the (reference) reservoir 14r can hold a calibration reagent that can be used to intermittently calibrate the mass scale of the mass spectrometer 75 (FIG. 12A,12B) that may provide greater mass accuracy for the sample material (e.g., analyte).

In some embodiments, a fluid junction 12j, 14j can be used to connect the transfer channels 12t, 14t and respective EO (electroosmotic) pump channels 22, 24. The fluid junctions 12j, 14j can be nanojunctions with the associated nanojunction channels having nanometer-sized depths. These channels also typically have micrometer-sized widths. The nanojunctions 12j, 14j can have, for example, a depth of about 50 nm and a width of about 50 μm. The depth of the nanochannel may be dictated by the ionic strength of the buffers used in the experiment/analysis and the corresponding Debye lengths. Nanochannel depth should be on the order of the Debye length or smaller.

However, it is also noted that the pumping elements can be provided in other ways including, for example, pressure driven flow with or without EO pump elements and the nanochannels are not required for such different pumping configurations. Examples of different flow/spray controls are further described below.

EO Pumping

The strategy for realizing an EO pump on a microchip for electrospray ionization can take forms other than shown in FIG. 1. The basic requirement is to have two channels intersect at a junction, which may be a T-like junction (not restricted to a right angle intersection). A voltage is applied to two of the three resulting channel termini generating an axial electric field through the associated channel segments. To realize hydraulic transport through the third channel segment, the electroosmotic mobility in the two channel segments that contain the axial electric field must be different in magnitude and/or sign. The difference in electroosmotic mobility can be achieved by chemically modifying one, or both, of the associated channel segments so as to produce different surface charge densities and hence different electroosmotic mobilities. Electroosmotic mobility can also be modified by coating a channel wall with electrically neutral polymer films, thereby increasing the effective fluid viscosity within the electrical double layer at the wall. Another way to modify electroosmotic mobility is reduce one of the channel lateral dimensions to distances similar in magnitude to the Debye length of the solution being electroosmotically pumped. The described methods for modifying electroosmotic mobility may also be used in combination where desired. Methods for electroosmotic pumping are further described in U.S. Pat. No. 6,110,343.

External Pressure Source Connection

Figure 11A:
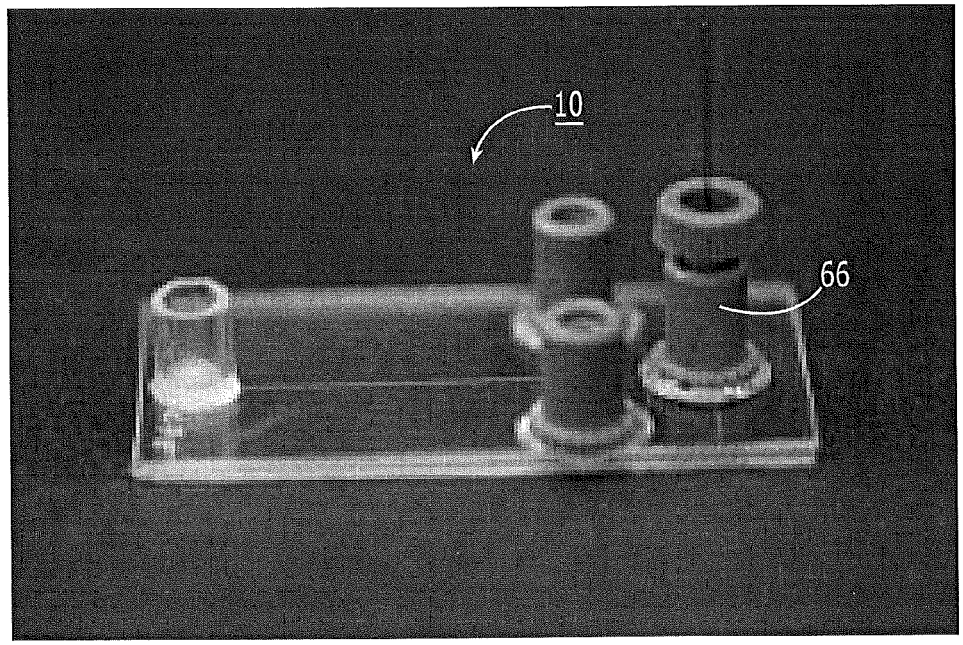
FIGS. 11A and 11B are digital photographs of exemplary microchips with fluid channels and examples of fluid connectors and inputs according to some embodiments of the present invention.
Figure 11B:
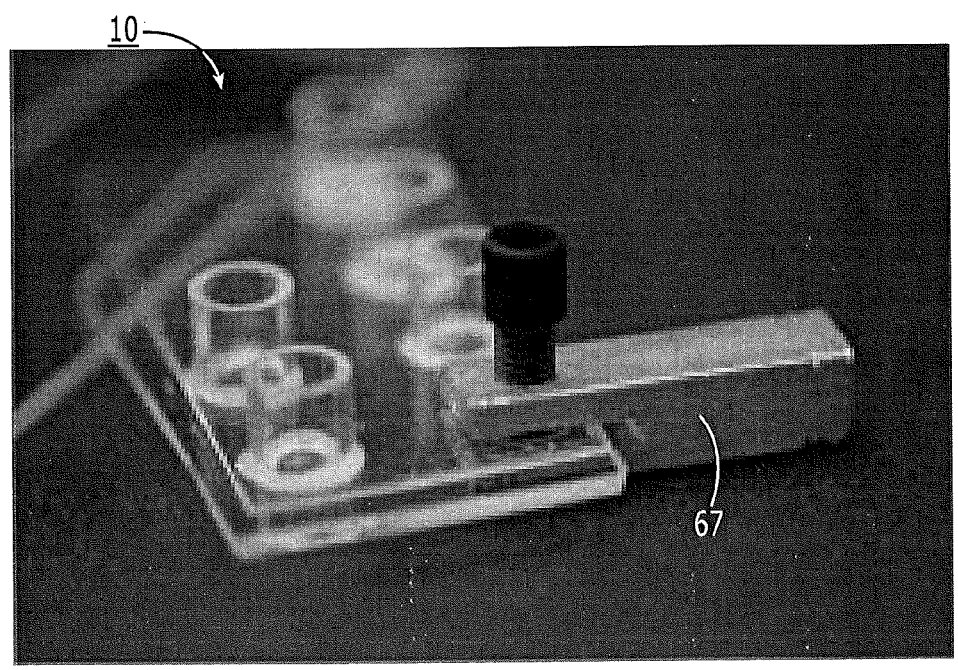

While it is convenient to monolithically integrate EO pump functional elements on electrospray microchip devices for delivering materials eluting from an electrokinetic separation channel to the electrospray emitter, it is possible to hydraulically deliver sample materials to the emitter. Various fluid delivery devices such as pneumatic bombs, piston pumps, syringe pumps, etc. can be connected to microchips 10 using tubing and connectors 66, 67 such as shown in FIGS. 11A and 11B, respectively. See, e.g., Chambers A G, Mellors J S, Henley W H & Ramsey J M (2011) Monolithic Integration of Two-Dimensional Liquid Chromatography—Capillary Electrophoresis and Electrospray Ionization on a Microfluidic Device. *Analytical Chemistry* 83, 842-849. When utilizing hydraulic transport to supply analyte to the emitter, electrical connection for producing the electrospray voltage can be achieved using a side channel similar to the EO pumping channel or by contacting the fluid using an electrode in a reservoir external to the chip, or in the case of using metal tubing between the microchip and the pump, connection can be made to the tubing.

Small Parallel Channels

Figure 10:
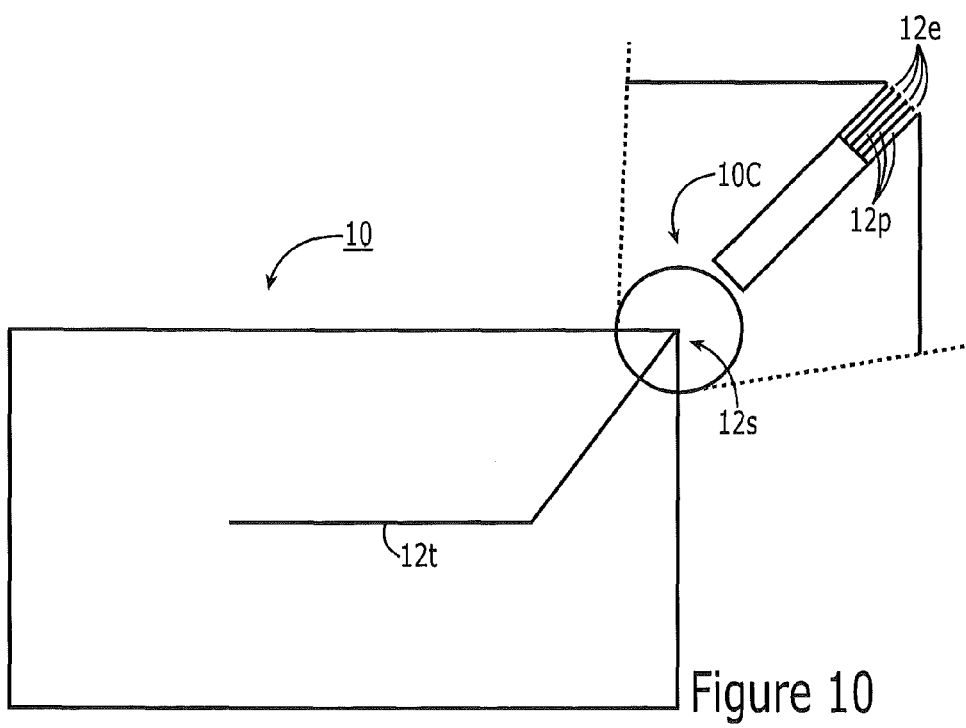
FIG. 10 is a top view of another microchip design according to embodiments of the present invention with an enlarged illustration of emitters on a corner of the microchip.

A multiemitter may also be formed by fabricating multiple parallel channels that lead to a planar edge formed on the microchip. The individual channels might be configured to have lateral dimensions of about 1 μm with spacings of about 50 μm. The individual channel dimensions could range from about 10 nm to a few microns and be spaced apart between about 1-100 μm. An example of a geometrical arrangement of such a device is shown in FIG. 10.

Where used, the reference material for the reference spray from a respective ESI emitter can provide one or more ions for internal calibration. In some embodiments, the reference material provides a single defined ion for internal calibration. In other embodiments, the reference material can include multiple ions over a desired range, typically that are over substantially an entire m/z range of interest, to improve the mass accuracy.

The reservoirs 12r, 14r, where used can be in fluid communication with an external fluid source to provide fluid thereto during analysis and/or the reservoirs 12r, 14r may be pre-loaded prior to active analysis.

Rapid modulation between the emitters 12, 14 can be accomplished by turning on and off voltage that simultaneously controls the ESI flow rate and ESI potential. The time required to switch between the two electrospray signals (reference versus analyte) can be less than about 100 ms, typically between about 1 ms to about 70 ms. The second emitter can spray the same or different analyte, and as discussed above, may be configured to introduce a reference material for internal calibration that can improve the accuracy of mass measurements (<3 ppm mass error).

As shown in FIG. 1, the EO pump channels 22, 24 can have a respective peak portion 22p, 24p that separates two elongate straight legs 221, 241, e.g., the EO pump channels can be substantially "U" or "V" shaped. The peak portion 22p, 24p can reside closer to the emitter 12, 14 than the legs. The legs 221, 241 can face the other end of the microchip in a direction that is toward a respective transfer channel 12t, 14t.

In some embodiments, the microchip 10 is a glass microfluidic device with at least two monolithic independent electrospray ionization (ESI) emitters 12, 14. The emitters 12, 14, can be operated to sequentially introduce ions from two solutions into the mass spectrometer 75 (FIG. 12A,12B) using integrated ESI interfaces. Fully integrated microchip ESI interfaces have been used for CE-MS analysis of standard protein digests and single cells. See, e.g., Mellors, J. S.; Gorbounov, V.; Ramsey, R. S.; Ramsey, J. M., Fully integrated glass microfluidic device for performing high-efficiency capillary electrophoresis and electrospray ionization mass spectrometry. *Anal. Chem*, 2008, 80, 6881; and Mellors, J. S.; Jorabchi, K.; Smith, L. M.; Ramsey, J. D. Integrated Microfluidic Device for Automated Single Cell Analysis Using Electrophoretic Separation and Electrospray Ionization Mass Spectrometry, *Anal. Chem.* 2010.

In some embodiments, at least two CE-ESI fluid reservoirs 12r, 14r, channels 12t, 14t, EO pumps 22, 24, and emitters 12, 14, are combined on a single microchip 10 and used to concurrently or sequentially introduce analyte and reference solutions. Although the alternating (sequential) operation is described primarily below, concurrent operation may also be possible. Further, spray from the emitters 12, 14 with infusion ESI-MS is primarily described herein, but integration with electrokinetically-driven separations is believed possible. Embodiments of the invention provide a very rapid analysis protocol at which two solutions can be analyzed with accurate sensitivity of a sequentially operated, multi-emitter configuration.

FIG. 1 also illustrates that the device 10 can include optional respective on-board channels 32, 34 for valving, each with a buffer and waste reservoir.

Figure 12A:
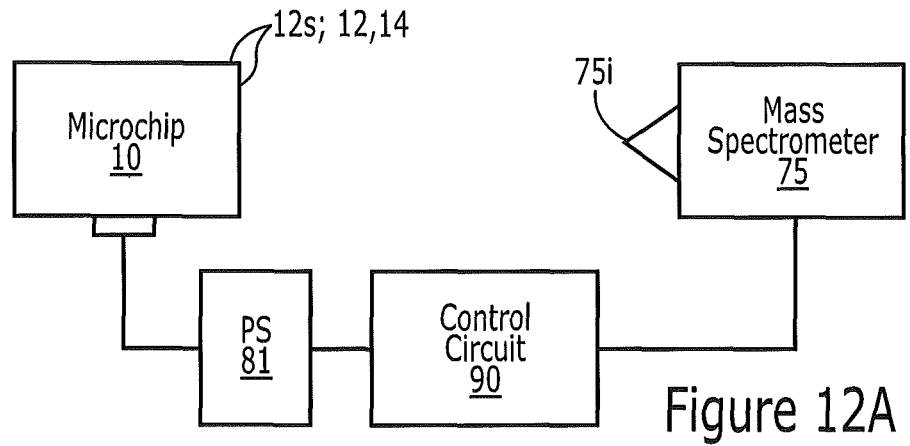
FIGS. 12A and 12B are schematic illustrations of examples of respective analyzer systems according to embodiments of the present invention.
Figure 12B:
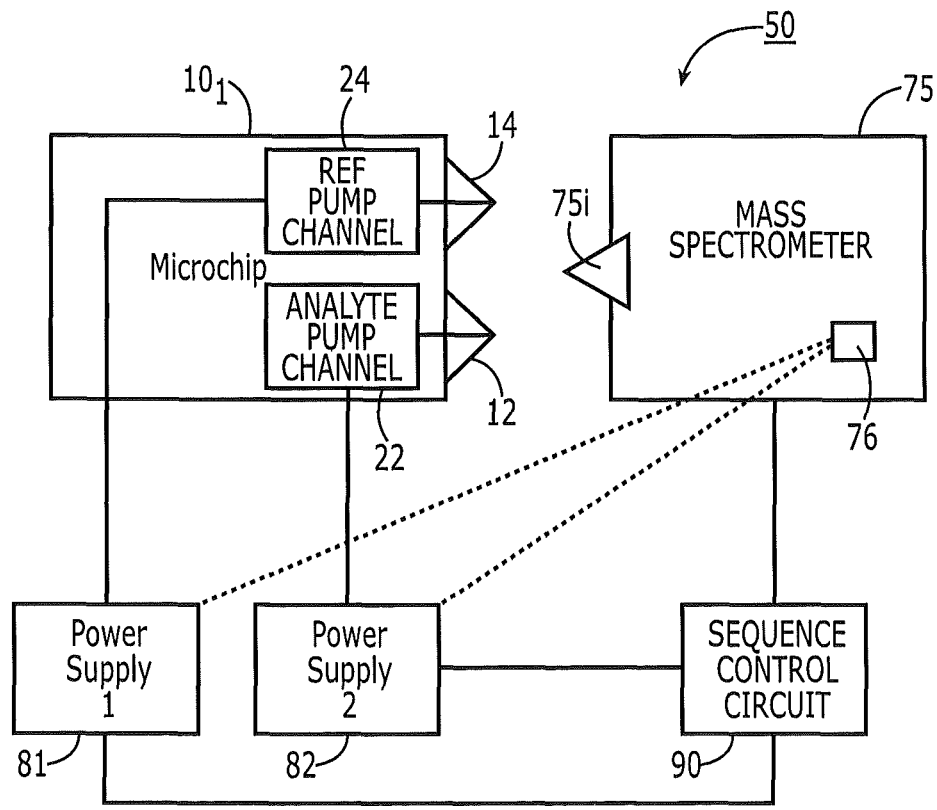

The microchip 10 can be held in a frame or other mounting device (not shown) that releasably holds the device 10 so that the emitters 12, 14 are in alignment with the spectrometer inlet 75i (FIG. 12B).

Still referring to FIG. 1, the emitters 12, 14 can have respective pointed substantially planar spray tips 12e, 14e that can be separated a distance "x". This distance is typically between about 0.1-6 mm, and in some embodiments is about 3.6 mm. The device 10 can have a gap space 10g. The gap space 10g can define an open space in the microchip body that extends between adjacent emitters 12, 14. A similar sized gap space can extend between the EO pump channel peaks 22p, 24p as shown in FIG. 1.

The transfer channels 12t, 14t can be configured so that the channels angle toward each other proximate the emitters 12, 14. In other embodiments, the channels are parallel through to the emitter tips. The electrospray direction can be determined by the electric field lines between the emitters and the inlet of the mass spectrometer. If appropriate voltages are applied, the fluid should be electrosprayed toward the inlet of the mass spectrometer. As shown in FIG. 1, the respective emitters 12, 14 can be configured so (in some embodiments, sequentially) that virtual extensions of the channels intersects at location "20" a distance "d" beyond the tip of the emitters 12, 14. Both ESI emitters 12, 14 can be aligned an equal distance (e.g., about 1.8 mm when spaced about 3.6 mm apart) from the axis of the mass spectrometer inlet orifice 75i (FIG. 12B) so that no movement of the spectrometer 75 or device 10 is required during data collection. In some embodiments, where the device includes the gap 10g, the centerline 10C$_L$ of the microchip 10 and/or the gap space 10g can be aligned with the axis of the mass spectrometer inlet orifice 75i. In other embodiments, the emitter tips are offset from the axis of the spectrometer, one more than another.

In some embodiments, the distance "d" is between about 1 mm to about 10 mm. Optionally, the flow rate may be between about 1 mL/min to 1000 mL/min. The microfluidic channel can have a width between 10 μm and 100 μm and a depth between 5 μm and 40 μm, however other channel dimensions may be used.

The microchip 10 can have a perimeter side that angles from an outer edge to a medial portion at the emitters 12, 14. The angle α can be between about 30-80 degrees, and may be between about 50-75 degrees.

The voltage at the emitter tip 12, 14 during an active or "on" state that causes the spray emission can be between about 1-3 kV. This voltage at the tip is only a fraction of the voltage applied to the EO pump channel reservoir due to the voltage dropped across the EO pump channel, e.g. 4.8 kV at the EO pump channel may result in 2.4 kV at the emitter tip. During an "off" state a small voltage may be applied to the respective EO pump channel (which is less than an amount that would cause electrospray discharge), but typically no (e.g., 0 kV) voltage is applied. The analyte and reference reservoirs 12r, 14r, can be held at a voltage for creating both the appropriate axial electric field strength in transfer channels 12t, 14t and the desired emitter voltage and can include ground potential. In some embodiments, no electrical connection to the buffer and waste channels are required when they are not utilized (e.g., in infusion analysis).

The operation of electroosomtically pumped electrospray interfaces have been described in U.S. Pat. No. 6,110,343, the content of which is hereby incorporated as if recited in full herein. See also, Ramsey R S & Ramsey J M (1997) Generating Electrospray from Microchip Devices Using Electroosmotic Pumping. *Anal Chem* 69, 1174-1178 and Mellors, J. S.; Gorbounov, V.; Ramsey, R. S.; Ramsey, J. M., Fully integrated glass microfluidic device for performing high-efficiency capillary electrophoresis and electrospray ionization mass spectrometry, *Anal. Chem.* 2008, 80, 6881; and Mellors, J. S.; Jorabchi, K.; Smith, L. M.; Ramsey, J. M., Integrated Microfluidic Device for Automated Single Cell Analysis Using Electrophoretic Separation and Electrospray Ionization Mass Spectrometry, *Anal. Chem.* 2010. Briefly stated, the positively charged surface of the (PolyE-323) coated transfer channel 12t (or 14t) and the corresponding negatively charged EO pump channel 22 (or 24) results in EOF (electroosmotic flow) towards the junction 12j (or 14j) of these two channels. The confluence of these two flows creates a small pressure increase at their intersection that forces the fluid out of the corresponding integrated ESI tip 12 (or 14). The junction 12j (or 14j) between the transfer channel 12t (or 14t) and the U-shape EO pump channel reduces the EOF in the EO pump channel by creating electrical double layer overlap. See, Burgreen, D.; Nakache, F. R. Electrokinetic flow in ultrafine capillary slits. *J. of Phys. Chem.* 1964, 68, 1084; and Hu, J. S.; Chao, C. Y. H. A study of the performance of microfabricated electroosmotic pump. *Sens. Actuators, A: Phys.* 2007, 135, 273.

In operation, the emitters 12, 14 can spray at desired time intervals such as sequentially electrospray at between about 1-3 second intervals. The spectrometer can operate with a relatively fast data acquisition rate such as about 15 Hz. When one emitter is turned on, the other can be turned off and the switching can be carried out with a seamless transition (e.g., "on" and "off" are substantially instantaneous compared to spectral acquisition rates). In some embodiments, a mass spectrometer on-board circuit or electronic component, such as a mechanical shutter control, 76 (FIG. 12B) with a trigger voltage input can be used to trigger or switch the on/off status of each respective power supply/emitter.

The multiple sources, such as an analyte or "sample material" through a first emitter 12 and reference or "calibration reagent" through another emitter 14, can be used to introduce multiple distinct species into a mass spectrometer using electrospray ionization. The reference reagent can be used to intermittently electronically calibrate the mass scale to provide greater mass accuracy for the sample material.

It is believed that the microfluidic systems contemplated by embodiments of the invention have advantages over capillary-based systems, including the ability to independently control ESI flow rate and ESI potential. The ability to independently control ESI flow rate and ESI potential is an advantage over previous microfluidic systems such as, for example, gravity fed systems and work described by Dayon et al, in Multitrack Electrospray Chips, *J. Mass Spectrom.* 2006; 41: 1484-1490. Further, or alternatively, fluid flow can be started relatively simultaneously with the application of the ESI potential. This can result in a stable ESI-MS signal that can be obtained faster than previous devices. The microchip devices can improve the mass accuracy of microchip ESI-MS measurements by introduction of an internal standard. By this method, the signal from a reference material (reagent or compound) can be used to electronically correct for drift in instrument calibration over the course of the analysis.

The microchips 10 may also be used for multiple separations to be monitored with a single mass spectrometer for increased sample throughput. Alternatively, materials may be electro-sprayed onto a surface for subsequent analysis, such as for example, by matrix-assisted laser desorption ionization MS. Another embodiment involves electrospraying the same sample from multiple emitters to achieve enhanced sensitivity or increase signal.

Generally stated, embodiments of the invention can provide microchips that can provide one or more of the following: (a) accurate mass measurements (b) increased signal; (c) sequential sample input for high throughput analysis; (d) parallel input into multiple mass analyzers simultaneously for high throughput analysis.

The systems can be configured to apply a post-data collection correction algorithm using the internal calibration signal that is collected over time. This can be termed a "continuous masslock correction" using the reference ion(s) signal. The post-collection data correction algorithm may employ the same algorithm as in conventional spectrometers such as that provided by commercially available software (MassLynx v4.1, Waters Corp, Milford, Mass.), which provides algorithms used to process the data (data smoothing, centroiding, and/or masslock correction). The corrected measures can have greater accuracy than the uncorrected measures. The spectrometer or control circuit (or other system component(s)) can be configured to electronically store the reference signal data in a different electronic data file(s) from the analyze signal file(s) correlated for future use. In some embodiments, for a substantially continuous masslock correction, the data can be first smoothed (twice by Savitzky-Golay, 4 chan-nels) and centroided (top 80% of peak). The number of lockspray (reference) scans can be any suitable number, typically about 10 (average).

In some embodiments, fewer reference scans can be obtained relative to the analyte scans, e.g., 1 reference scan about every 3-5 seconds.

FIGS. 2A and 2B illustrate that the microchip 10 includes a first substantially rigid substantially planar substrate 10$f$ that is processed or formed to have the fluidic channels. The emitters 12, 14 are monolithic such that they are defined by shapes formed into the substrate(s). Stated differently, the emitters are formed directly into (are integral with) the substrate(s) without requiring additional components or materials. The at least two emitters 12, 14 are formed so that they project as shaped forms off at least one side or end of the microchip 10.

Examples of substantially rigid materials include, but are not limited to, substrates comprising one or combinations of: glass, quartz, silicon, ceramic, silicon nitride, polycarbonate, and polymethylmethacrylate. In particular embodiments, at least the first substrate 10$f$ can be glass such as a borosilicate. In other embodiments, a rigid polymer material may be used to form the microchip.

The microchip 10 can have a second substantially planar substrate 11 that can seal the fluidic channels on the first substrate 10$f$. The second substrate 11 can also be substantially rigid and can be a "blank" of the first substrate. The first and second substrates 10$f$, 11 may each be fabricated to include one or more of the fluidic channels with the other substrate forming the cover for the other. Alternatively, each may include partial channels that when assembled define cooperating portions of the respective fluidic channels. The second substrate 11 can have a thickness that is substantially the same (or less than that of the first substrate). However, it may also have a greater thickness than the formed substrate 10$f$. The first substrate 10$f$ typically has a thickness that typically ranges from between about 150-1000 µm. In some embodiments, the first and second substrates 10$f$, 11 can both comprise glass.

The second substrate 11 can be bonded to the other substrate 10$f$ to form a sealed cover over the fluid channels. Access ports or vias can be formed at desired segments of the channels, e.g., proximate the termini of the channels. See, e.g., Mellors, J. S.; Gorbounov, V.; Ramsey, R. S.; Ramsey, J. M., Fully integrated glass microfluidic device for performing high-efficiency capillary electrophoresis and electrospray ionization mass spectrometry. *Anal. Chem.* 2008, 80, 6881.

It is noted that either or both of the substrates 10$f$, 11 can be substantially planar multi-layer structures with a plurality of laminated or otherwise securely attached stacked layers. Further, although shown as two substrates in two layers, three or more substrates and/or layers may be used, e.g., 3, 4, 5, 6, 7, 8, 9, 10 and the like. Further, one substrate may be rigid and another may have less rigidity (e.g., be semi-rigid or flexible when not attached to the rigid substrate). Thus, for example, one substrate with the fluid channels 10$f$ may be glass that is sealed with a flexible or substantially rigid polymeric substrate 11.

FIGS. 3A-3B illustrate that the microchip 10 can be a stacked microchip 10, with at least two microchips $10_1$, $10_2$, such as two of the devices of FIG. 1, stacked one on top of the other. This embodiment provides multiple emitters in two planes, $12_1$, $12_2$, $14_1$, $14_2$ along a same side of the microchip 10$s$. As shown, emitters $12_1$, $14_1$ are in one plane while $12_2$, $14_2$ are in another. As before, $12_1$, $14_1$ are in the same plane. Pairs or one or several of the emitters can reside in different planes, parallel to other emitters above or below (e.g., $12_1$, $12_2$). A plurality of the emitters in the same or different planes can spray concurrently with the same material to increase signal intensity. FIG. 3C illustrates that two fluid-channel substrates can be sealed together with a "blank" substrate 11 therebetween while FIGS. 3A and 3B show that four substrates can be used.

In some embodiments, additional layer substrates of fluid channels can be stacked, such as 3-20, typically about 3-6 to form multiple layers of parallel emitter tips/nozzles in different planes. In some particular embodiments, the microchips 10 can include a first set of ESI emitters that can spray an analyte and a second different set of ESI emitters can spray a reference analyte. The emitters may be side-by-side or one above another or spaced apart side-to-side and timed to spray concurrently.

The stacked microchips 10s can have different fluidic channel arrangements. For example, one may include only one channel while another may include two or more channels. In one embodiment, one microchip 10 may include an analyte channel 12 (without a reference channel 14 or reference reservoir 14r) or two or more side-by-side analyte channels 12 on the same substrate (one in place of the reference channel 14) and the other may include only one reference channel 14 or a plurality of side by side reference channels 14. The device 10 can concurrently spray the analyte from more than one emitter to increase signal intensity.

FIGS. 4A and 4B illustrate another embodiment of the microchip 10. In this embodiment, four emitters $12_1$, $12_2$, $14_1$, $14_2$ are co-planar. Pairs of the emitters $12_1$, $12_2$, and $14_1$, $14_2$ may be configured to spray concurrently for signal detection by the spectrometer 75.

FIGS. 5A and 5B illustrate yet another embodiment of a microchip 10". In this embodiment, the microchip 10 can include a third monolithic emitter 15 with its respective transfer channel 15t and optional EO pump channel (not shown). The third emitter 15 may be configured with an optional separate reservoir or may be in fluid communication with the analyte reservoir 12r and may optionally be configured to concurrently spray analyte with the analyte emitter 12 to increase signal intensity. The center emitter 15 can have a tip that is recessed relative to the inner and outer emitters 12, 14 so as not to interfere with the spray plume from each of those emitters during active mode. Each emitter 12, 14, 15 may include the additional fluidic components shown for FIG. 1.

Figure 6B:
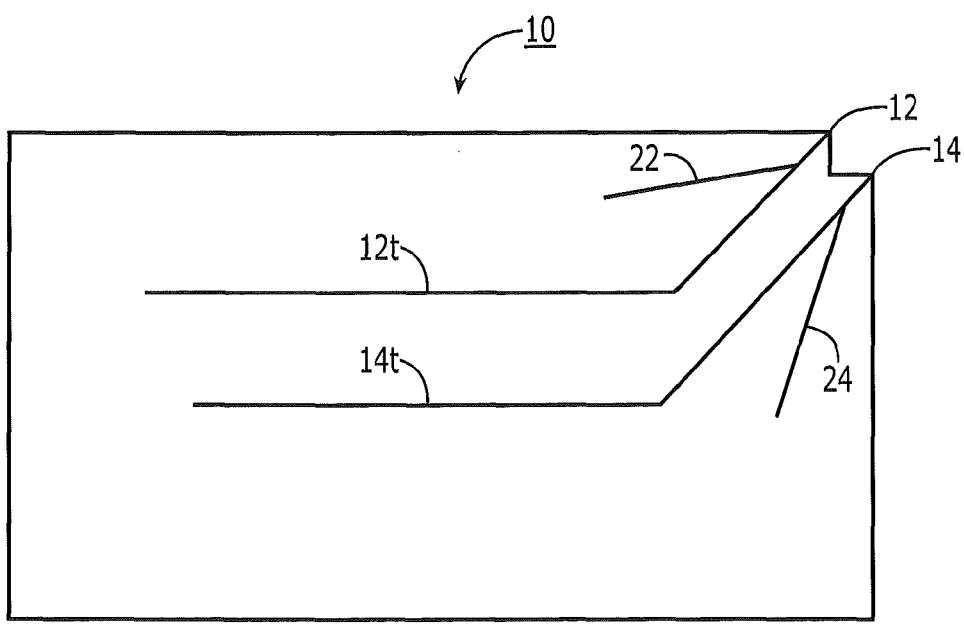
FIG. 6B is a top view of the microchip shown in FIG. 6A, illustrating the emitters with pump channels according to some embodiments of the present invention.

FIGS. 6A, 6B and 7-10 illustrate additional embodiments of the microchip 10. FIG. 6A illustrates two channels 12t, 14t, each extending to a respective ESI emitter 12, 14 on a corner 10c of the microchip 10. FIG. 6B illustrates pump channels 22, 24, such as EO pump channels or hydraulic-based pump channels. However, other flow control configurations may also be used.

Figure 7:
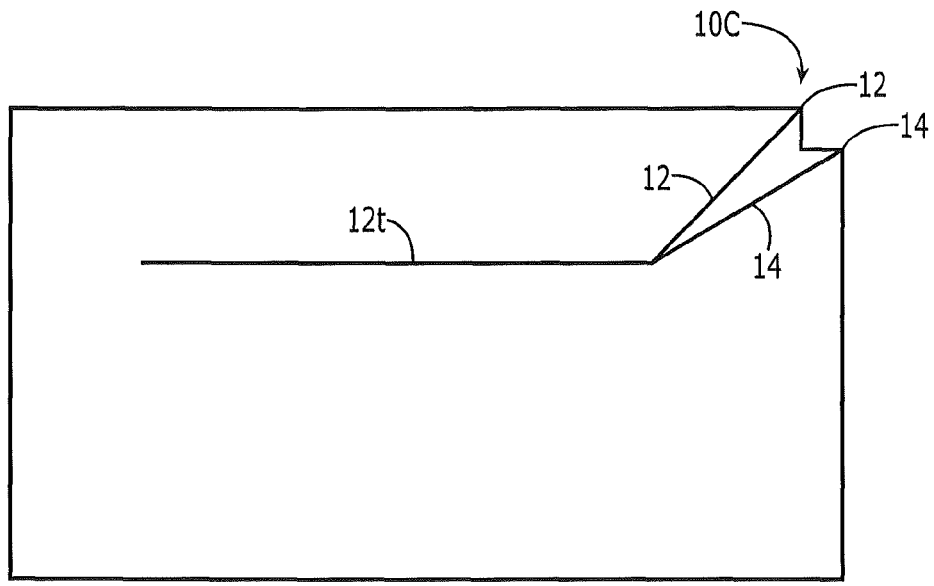
FIG. 7 is a top view of another microchip design according to embodiments of the present invention.

FIG. 7 illustrates a microchip 10 with corner ESI emitters 12, 14, but each of these ESI emitters 12, 14 can connect to a common channel 12t. The channel 12t can branch 12b at a location upstream of the corner 10c. Although not shown, pump channels, such as, for example, EO pump channels or hydraulic-based pump channels and/or electrical connection to other flow control circuits may be used.

Figure 8:
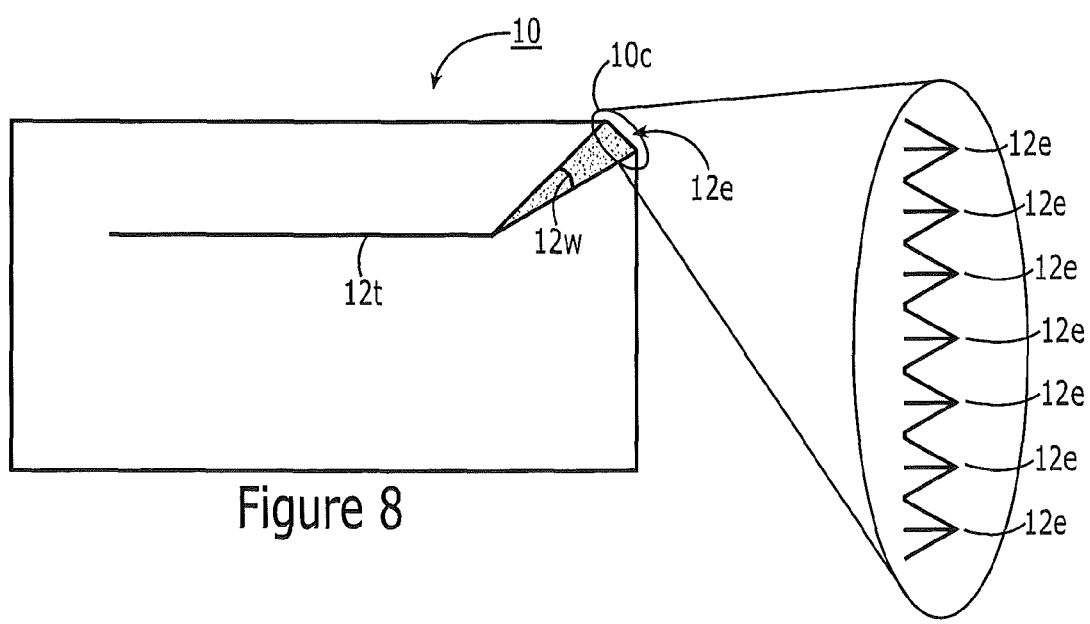
FIG. 8 is a top view of another microchip design according to embodiments of the present invention, with an enlarged illustration of emitters on a corner of the microchip.

FIG. 8 shows another embodiment of a microchip 10 with monolithic ESI emitters 12e on a corner 10c. A series of small sharply pointed ridges may form the ESI emitter(s) 12e. The emitters 12e may be closely spaced apart between about 1-50 µm. The number of ESI emitters 12e on the corner 10c may be between about 2-100, typically between about 4-100, such as between about 4-40 or 4-20. In some embodiments, the microchip can have between about 4-10 or 5-10 (shown as about 7) closely spaced emitters proximate one corner, but more may be used to enhance ESI signal. They may be equally spaced or asymmetrically arranged. The plurality of emitters 12e can communicate with a single fluid transfer channel 12t. Alternatively, the plurality of emitters 12e can communicate with a plurality of channels, typically where the number of channels 12t is equal to or less than the number of emitters 12e. Although not shown, pump channels such as EO pump channels or hydraulic-based pump channels and/or electrical connection to other flow control circuits may be used.

Figure 9:
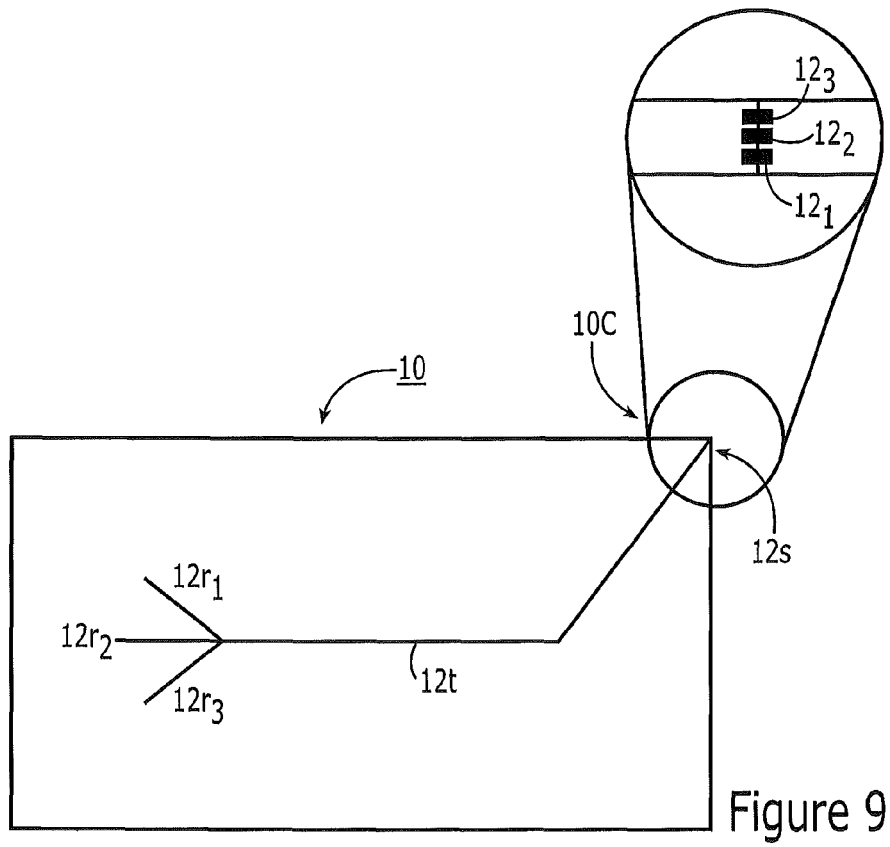
FIG. 9 is a top view of another microchip design according to embodiments of the present invention with an enlarged illustration of emitters on a corner of the microchip.

FIG. 9 illustrates a set of stacked emitters 12s arranged on a corner of the microchip 10. As shown, there are three stacked emitters $12_1$, $12_2$, $12_3$, but two or four or more may be provided, e.g., 2-100, 4-100, and typically between about 2-20 layers of emitters with one or more emitter per layer forming between about 2-100 emitters, such as, for example, between about 4-40, 4-20, 4-10 and 5-10 emitters. The emitters 12s can be fed by separate channels formed in the appropriate substrate and may be fed by a common reservoir 12r or different reservoirs $12r_1$, $12r_2$, $12r_3$, or some emitters may share some reservoirs. Vias can be drilled into the substrates to provide fluid communication with a desired reservoir and/or channel, e.g., to communicate with the fluid channels on different substrates. Although not shown, pump channels such as EO pump channels or hydraulic-based pump channels and/or electrical connection to other flow control circuits may be used.

FIG. 10 also illustrates a microchip 10 with a plurality of parallel emitters 12s on a corner 10c. Again, the plurality of emitters proximate the corner can be between about 2-100 emitters, typically between about 4-100. The emitters can be closely spaced and provided in a number that is between about 4-40 or between about 4-20 (e.g., 4-10, 6-10). The microchip 10 can include a plurality of closely spaced substantially parallel fluid channels 12p that merge into respective emitters 12e. The fluid channels 12p and emitters 12e may be closely spaced apart between about 1-50 µm. The fluid channels 12p may communicate with a common upstream feeder channel 12t, or different feeder channels. The feeder fluid channels 12t can either utilize separate and distinct reagent reservoirs, or a common reservoir. Although not shown, pump channels such as EO pump channels or hydraulic-based pump channels and/or electrical connection to other flow control circuits may be used.

Note that for all microchips 10 described and shown herein, a substrate can be processed and/or machined on both sides (primary surfaces) to include channel features or only one side.

FIG. 12A illustrates that an analyzer system 50 that may include a control circuit 90 in communication with the mass spectrometer 75 and microchip 10 and at least one power supply 81 in communication with the microchip 10. For illustration only, the microchip 10 is shown with the corner 10c emitters 12s or 12, 14. Other embodiments of the microchip may be used. The control circuit 90 can synchronize fluid transport through the microchip 10 with data acquisition by the mass spectrometer 75. The control circuit 90 may cause different emitters to sequentially spray or spray concurrently. In some particular embodiments, the control circuit 90 can direct one or a first set of ESI emitters to spray an analyte then direct one or a second different set of ESI emitters to spray the reference analyte.

FIG. 12B illustrates an exemplary analysis system. The system 50 includes the microchip 10, 10s aligned with an inlet 75i of a mass spectrometer 75. For illustration only, the medially positioned ESI emitters 12, 14 are shown. Other embodiments of the microchip 10, such as those shown and/or described herein, may be used. The at least one power supply, shown as power supplies 81, 82 are in communication with the emitters 12, 14, via EO pump channels 24, 22 or to another input associated with the microchip for controlled flow as described above. The system 50 includes a sequence control circuit 90 that can control the operation of the mass spectrometer 75 and sequence of operation of the emitters 12, 14. The control circuit 90 can reside partially or totally in the mass spectrometer 75 and/or reside in one or more external local or remote processors that can be hard wired or wirelessly communicate with the power supplies 81, 82 and/or mass spectrometer 75. The control circuit 90 can be configured to use an on-board circuit or electrical component to provide the synchronized operation. For example, the system 50 may use the mass spectrometer on-board shutter trigger voltage circuit or a different circuit with a different trigger or synchronization protocol. In particular embodiments, the mass spectrometer 75 may optionally include a mechanical baffle switch and circuitry 76 that forms part of the control circuit 90 and/or is used to synchronize the activation/deactivation of power supplies 81, 82.

Figure 13:
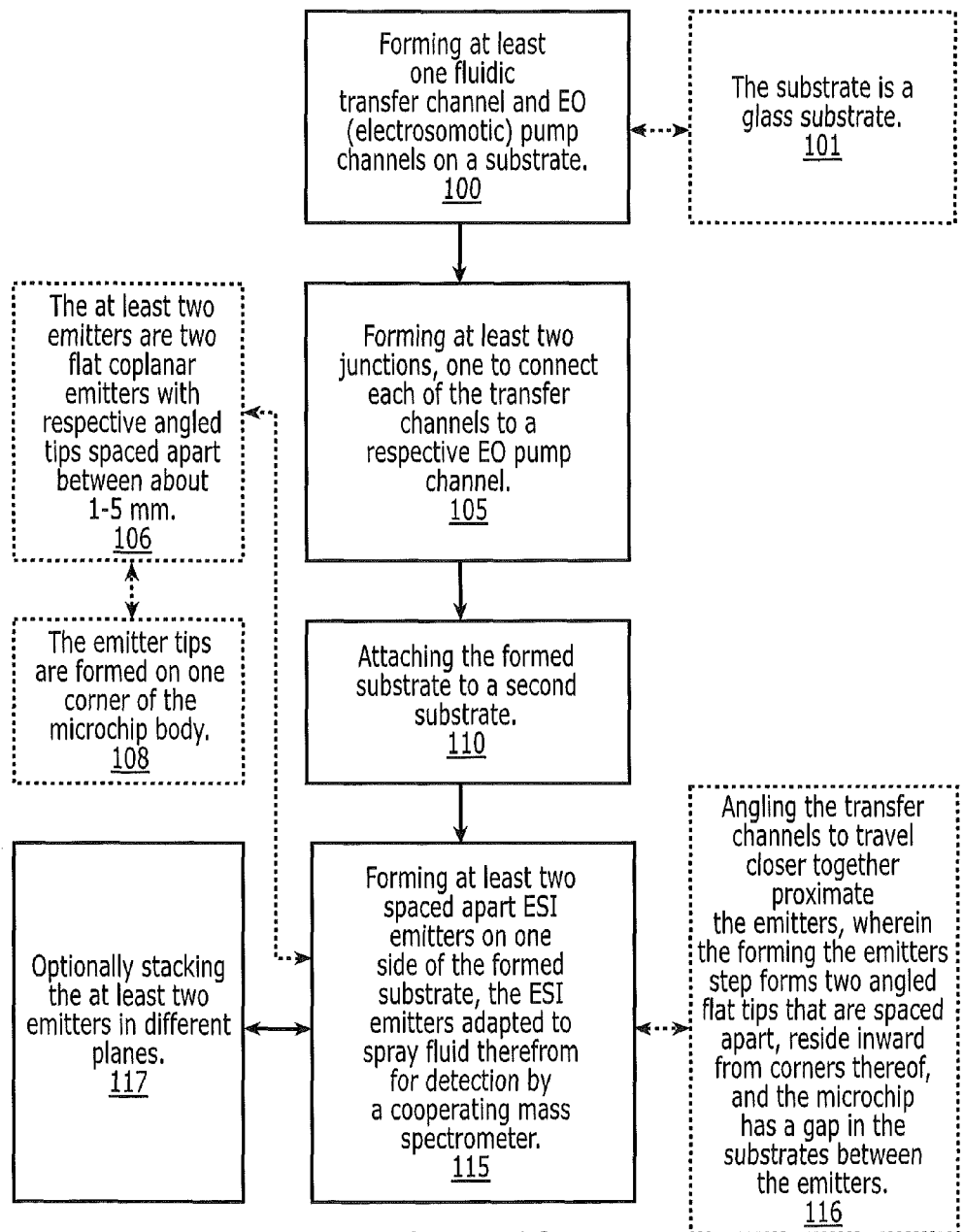
FIG. 13 is a flow diagram of exemplary fabrication steps according to embodiments of the present invention.

Embodiments of the invention are directed to methods of forming microchips and may include exemplary steps shown, for example, in FIG. 13. At least one fluidic transfer channel (and optionally EO (electrosomotic) pump channels) can be formed on a (substantially planar, rigid) substrate (block 100). The microchip fluid channel(s) (e.g., 12t, 14t) can be formed via conventional photolithographic patterning and wet-chemical etching and the like. As noted above, the substrate may optionally be a glass substrate (block 101).

Where used, junctions connecting the transfer channels to a respective BO pump channel can be formed (block 105). This step may be carried out via milling and/or wet-etching at least two nanojunctions, one to connect each of the transfer channels to a respective EO pump channel. The formed substrate can then be attached to a second substrate (block 110) to seal the channels on the first substrate. At least two spaced apart ESI emitters can be formed on one side of the formed substrate (inward from opposing corners thereof), the ESI emitters adapted to spray fluid therefrom for detection by a cooperating mass spectrometer (block 115).

The electrospray tip emitters can be machined after the substrates are bonded by dicing the bonded microchip with a precision dicing saw (Dicing Technology, San Jose, Calif.) or by laser or other precision cutting. The microchip body can be shaped to form the desired nozzle/emitter tip. Grinding or lapping procedures could be used to further shape the tip if desired.

The at least two emitters can be two flat coplanar emitters with respective angled tips spaced apart between about 0.1-5 mm (block 106) The coplanar emitters can be formed proximate on one corner of the microchip body (block 108). The transfer channels can be configured to have an angle to travel closer together proximate the emitters relative to their alignment and position upstream thereof, wherein the step of forming the emitters forms two angled tips that are closely spaced apart and the microchip has a gap in the substrates between the emitters (block 116).

The method may also optionally include stacking at least two of the formed substrates onto each other to provide at least four emitters in different planes (block 117).

As noted above, the junctions may be formed by milling and/or wet chemical etching or photolithography as described above with respect to the transfer channels. The term "milling" refers to any process that forms channels using a charged particle or particles. Alternatively the channel features could be formed in polymeric materials, or any material that is plastic, using embossing or molding techniques. Moreover, channel features could be cut using laser-based machining methods into any material that can be ablated using appropriate laser energy. Materials that can be laser machined include glasses, plastics and co-fired ceramics.

Figure 14:
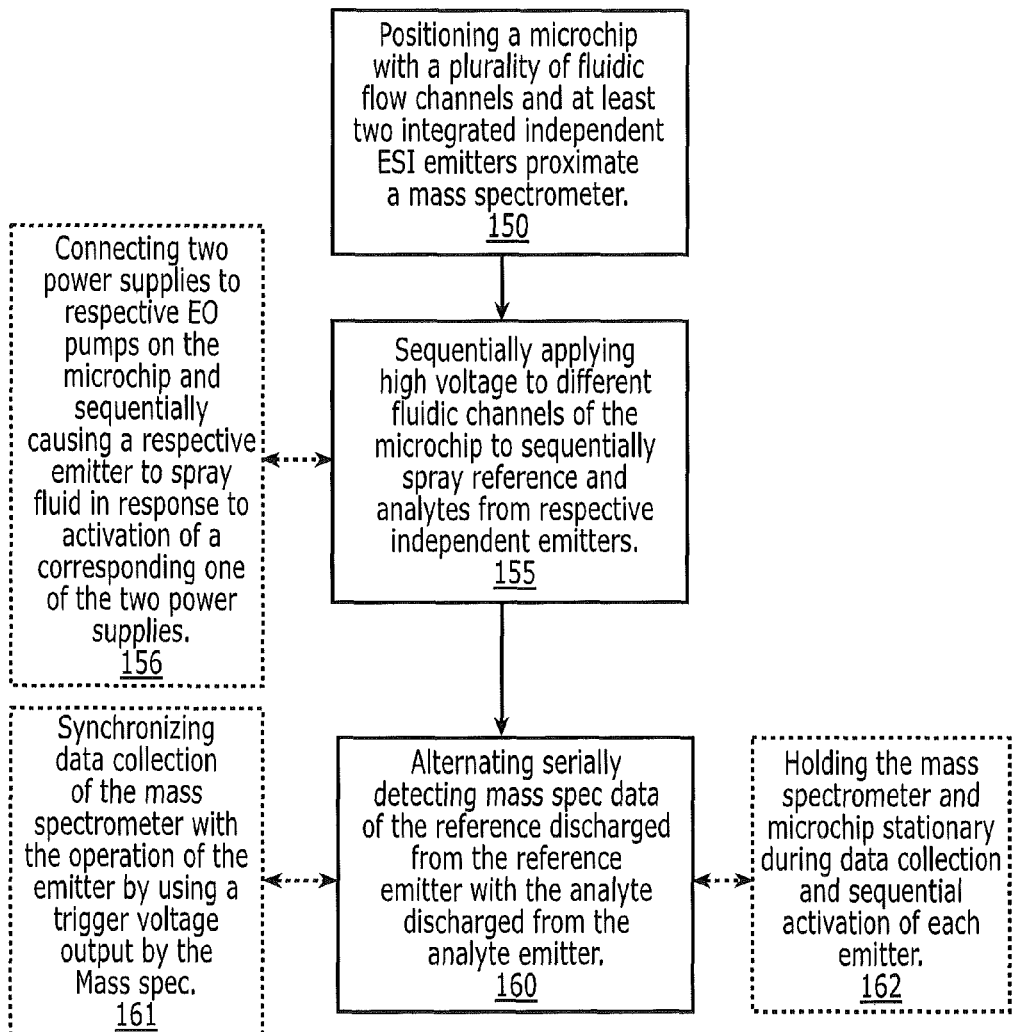
FIG. 14 is a flow chart of exemplary operational steps that can be used to collect mass spectrometer data according to embodiments of the present invention.

FIG. 14 illustrates exemplary steps for collecting mass spectrometer data. As shown, a microchip with a plurality of fluidic flow channels and at least two integrated independent ESI emitters are positioned proximate a mass spectrometer inlet (block 150). High voltage can be sequentially applied to the different fluidic channels of the microchip to sequentially spray reference and analyte from respective independent emitters (block 155). Mass spectrometry data for the reference material discharged from the reference emitter is alternately serially detected with the analyte discharged from the analyte emitter (block 160).

Before the detecting step, the method can include connecting two power supplies to respective EO pumps on the microchip and sequentially causing a respective emitter to spray fluid in response to activation of a corresponding one of the two power supplies (block 156).

Optionally, the data collection of the mass spectrometer can be electronically synchronized with the operation of the emitter by using a trigger voltage output associated with a mechanical baffle circuit onboard the mass spectrometer (block 161).

Both the mass spectrometer and the microchip can be held stationary during data collection and sequential activation of each emitter (block 162).

It is noted that embodiments of the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on the user's computer, partly on the user's computer, as a stand-alone software package, partly on the user's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

Embodiments of the present invention are described herein, in part, with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, or a block divided and performed separately, depending upon the functionality involved.

Figure 15:
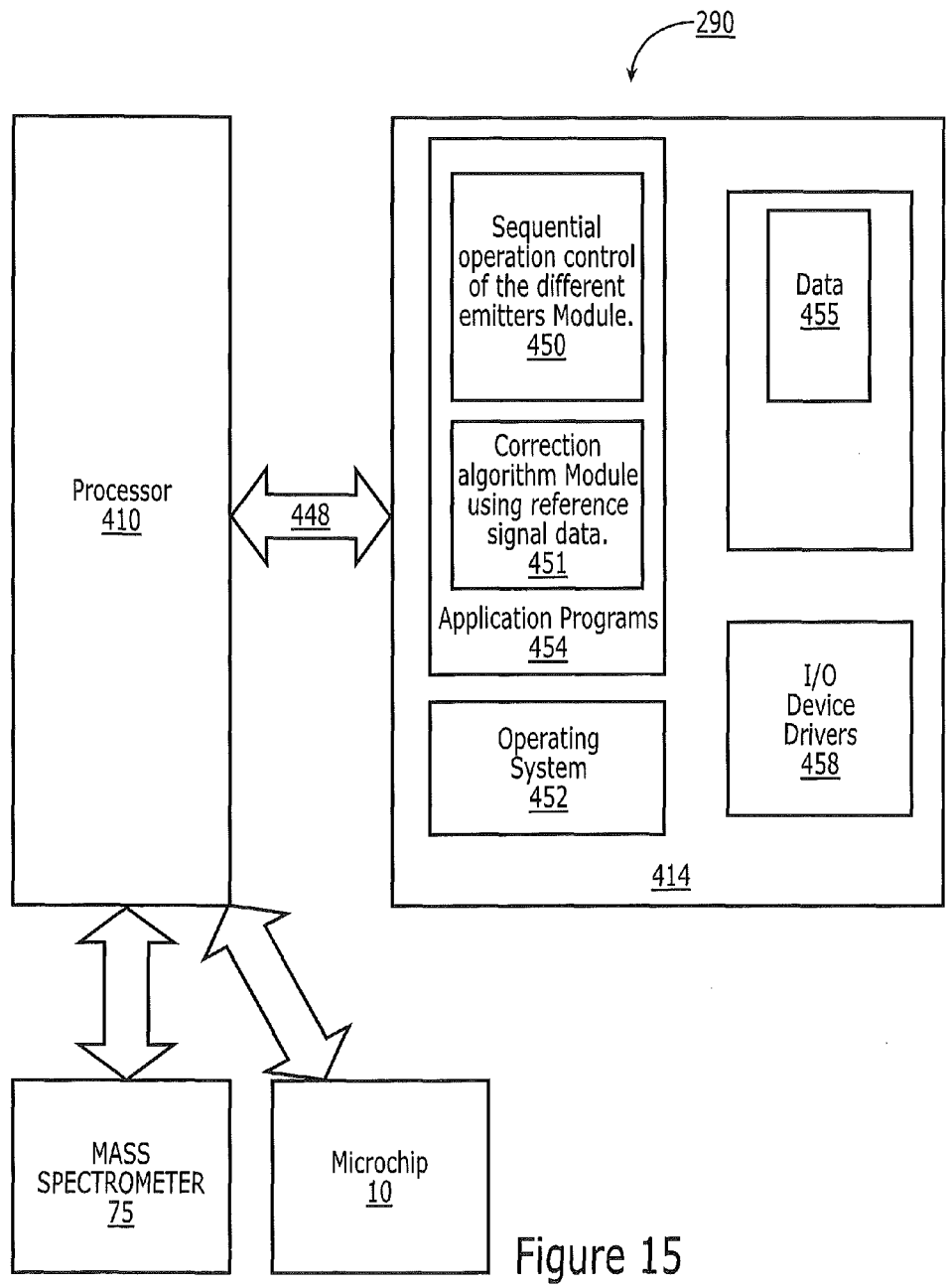
FIG. 15 is a block diagram of a data processing system according to embodiments of the present invention.

FIG. 15 is a schematic illustration of a circuit or data processing system 290. The system 290 can be used with any of the microchips 10 and/or mass spectrometers 75. The circuits and/or data processing systems 290 may be incorporated in a digital signal processor in any suitable device or devices. As shown in FIG. 15, the processor 410 can communicate with a mass spectrometer 75 and/or microchip 10, 10s and with memory 414 via an address/data bus 448. The processor 410 can reside in a control circuit 90 (FIG. 12) that is separate from the spectrometer 75 or that is integrated wholly or partially therein. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

FIG. 15 illustrates that the memory 414 may include several categories of software and data used in the data processing system: the operating system 452; the application programs 454; the input/output (I/O) device drivers 458; and data 455. The data 455 can include calibration data, time synchronization data (e.g., trigger voltage data), and/or other detected or internal mass spectrometer data.

As will be appreciated by those of skill in the art, the operating systems 452 may be any operating system suitable for use with a data processing system, such as OS/2, AIX, DOS, QS/390 or System390 from International Business Machines Corporation, Armonk, N.Y., Windows CE, Windows NT, Windows95, Windows98, Windows2000, WindowsXP or other Windows versions from Microsoft Corporation, Redmond, Wash., Unix or Linux or FreeBSD, Palm OS from Palm, Inc., Mac OS from Apple Computer, LabView, or proprietary operating systems. The I/O device drivers 458 typically include software routines accessed through the operating system 452 by the application programs 454 to communicate with devices such as I/O data port(s), data storage 455 and certain memory 414 components. The application programs 454 are illustrative of the programs that implement the various features of the data (image) processing system and can include at least one application, which supports operations according to embodiments of the present invention. Finally, the data 455 represents the static and dynamic data used by the application programs 454, the operating system 452, the I/O device drivers 458, and other software programs that may reside in the memory 414.

While the present invention is illustrated, for example, with reference to the Sequential Operation Control and Correction Modules 450, 451 being an application program in FIG. 15, as will be appreciated by those of skill in the art, other configurations may also be utilized while still benefiting from the teachings of the present invention. For example, the Module 450 and/or 451 may also be incorporated into the operating system 452, the I/O device drivers 458 or other such logical division of the data processing system. Thus, the present invention should not be construed as limited to the configuration of FIG. 15, which is intended to encompass any configuration capable of carrying out the operations described herein. Further, Module 450 and/or 451 can communicate with or be incorporated totally or partially in other components, such as a mass spectrometer 75, power supply, an interface/gateway or a computer such as at a workstation that may be local or remote from the microchip/spectrometer.

The I/O data port can be used to transfer information between the data processing system, the workstation, the spectrometer, the microchip, the interface/gateway and another computer system or a network (e.g., the Internet) or to other devices or circuits controlled by the processor. These components may be conventional components such as those used in many conventional data processing systems, which may be configured in accordance with the present invention to operate as described herein.

The present invention is explained in greater detail in the following non-limiting Examples.

EXAMPLES

Experimental

Reagents. Deionized, filtered water was used in an experiment (Nanopure Diamond, Barnstead International, Dubuque, Iowa). A PolyE-323 polymer was synthesized as previously described from 1,2-bis(3-aminopropylamino)ethane and epichlorohydrin that were both obtained from Sigma Chemical Co. (St. Louis, Mo.). See, Hardenborg, E.; Zuberovic, A.; Ullsten, S.; Soderberg, L.; Heldin, E.; Markides, K. E. Novel polyamine coating providing non-covalent deactivation and reversed electroosmotic flow of fused-silica capillaries for capillary electrophoresis. *J. Chromatogr. A* 2003, 1003, 217. The PolyE-323 solution was adjusted to pH of 7 with acetic acid (Fisher Chemical, Fairlawn, N.J.) and diluted with water to 15% (by mass) polymer. The electrospray solutions were 2 µM reserpine (Sigma Chemical Co.) or 2.5 µM leucine enkephalin (American Peptide Co., Inc., Sunnyvale, Calif.) in an aqueous solution with 0.1% (v/v) formic acid (99%, Sigma Chemical Co.) and 50% acetonitrile (HPLC grade, Fisher), pH 2.9. The trichloro(1H, 1H,2H,2H-perfluorooctyl)silane was also acquired from Sigma Chemical Co. All other reagents were analytical grade and used without further purification.

Microchip Fabrication. The channel layout for an exemplary microchip dual ESI device is shown in FIG. 1. Microchannels were fabricated into 150 µm thick glass substrates (Corning 0211 borosilicate, Erie Scientific Co., Portsmouth, N.H.) by standard photolithography, wet-chemical etching procedures. See, Mellors, J. S.; Gorbounov, V.; Ramsey, R. S.; Ramsey, J. M., Fully integrated glass microfluidic device for performing high-efficiency capillary electrophoresis and electrospray ionization mass spectrometry. *Anal. Chem.* 2008, 80, 6881. The depth and full width of the channels were measured with a profilometer (P15, KLA-Tencor Corp., San Jose, Calif.) to be 8 µm and 60 µm, respectively. The lengths of the channels were as follows: analyte and reference 5 mm, buffer and waste 14 mm, transfer 42 mm, and U-shaped electroosmotic (EO) pump 12 mm. A nanojunction with dimensions 50 nm deep and 50 µm wide was created by focused ion beam milling (FEI Helios Nanolab 600, Hillsboro, Oreg.) to connect the 75 µm gap between the U-shaped (EO) pump channel and the transfer channel. Access ports were powder blasted (Comco, Inc., Burbank, Calif.) at the termini of the channels and a blank substrate was fusion bonded to the etched substrate as previously described. Mellors et al., *Anal. Chem.* 2008, Id. The electrospray tip was machined by dicing the bonded microchip with a precision dicing saw (Dicing Technology, San Jose, Calif.) so that the transfer channels terminated at about 50° edges. The distance between the electrospray tips was 3.6 mm. The surface of all channels except the EO pump channels was coated with PolyE-323 as previously described. PolyE-323 is a polyamine that adheres to glass surfaces through electrostatic and hydrogen bonding forces to provide stable anodic (reversed) electroosmotic flow (EOF) when using a neutral to acidic background electrolyte. In addition, the exterior of the electrospray tips were coated with a perfluorooctylsilane, which made the surface hydrophobic to prevent wetting. See, Mellors, J. S.; Jorabchi, K.; Smith, L. M.; Ramsey, J. M., Integrated microfluidic device for automated single cell analysis using electrophoretic separation and electrospray ionization mass spectrometry. *Anal. Chem.* 2010, 82, 967.

Microchip Operation. Infusion of analyte and reference materials was accomplished by applying electric potentials to select reservoirs to generate EOF within the device. Electric potentials were applied using two independent power supplies (2866A; Bertan, Hicksville, N.Y.) that had voltage rise and fall times of approximately 5 ms. The power supplies were computer-controlled using an analog output board (PCI-6713, National Instruments, Austin, Tex.) and LabVIEW software (version 8.5, National Instruments). High voltage was applied to the U-shaped EO pump reservoir located closer to the ESI spray tip. Typical voltages applied to this reservoir during the "off" and "on" states were approximately 0 kV and +4.8 kV, respectively. The analyte and reference reservoirs were held at ground. No electrical connection was made to the buffer and waste channels as they were not utilized in these infusion experiments. The operation of the electroosmotically pumped electrospray interface has been described. Mellors et al., *Anal. Chem.* 2008, Id. An x-y-z translational stage was used to position the microchip emitters approximately 5 mm from the plane of the mass spectrometer inlet orifice. Both ESI emitters were aligned an equal distance (1.8 mm) from the axis of the mass spectrometer inlet orifice unless otherwise stated and the device remained stationary during all experiments. The electrospray plumes were illuminated using separate green diode lasers and imaged using a zoom lens (VZM 450, Edmund Optics, Barrington, N.J.) and CCD camera at 30 fps. MS data was acquired using a quadrupole time-of-flight (QT of) mass spectrometer (Micromass QT of Micro, Waters Corp., Milford, Mass.) except as indicated in the text where a T of mass spectrometer (LCT-Premier, Waters Corp.) was utilized for its faster data acquisition rate. Data were acquired by the QT of using 1 s summed scans and an interscan delay of 0.1 s whereas the T of acquired data were collected using 0.05 s summed scans and an interscan delay of 0.01 s. Both MS instruments were configured to acquire spectra over an m/z range of 100-1000. For accurate mass measurements, the switching of the electrospray signals was synchronized with the data acquisition on the QT of instrument. The instrument software (MassLynx version 4.1, Waters Corp.) was originally designed to control the baffle position in the commercial dual ESI source (NanoLockSpray, Waters Corp.) to select the analyte or reference electrospray signal. See, e.g., Eckers, C.; Wolff, J. C.; Haskins, N.J.; Sage, A. B.; Giles, K.; Bateman, R., Accurate mass liquid chromatography/mass spectrometry on orthogonal acceleration time-of-flight mass analyzers using switching between separate sample and reference sprays: (1) Proof of concept. *Anal. Chem.* 2000, 72, 3683; and Wolff, J. C.; Eckers, C.; Sage, A. B.; Giles, K.; Bateman, R., Accurate mass liquid chromatography/mass spectrometry on quadrupole orthogonal acceleration time-of flight mass analyzers using switching between separate sample and reference sprays: and (2) Applications using the dual-electrospray ion source. *Anal. Chem.* 2001, 73, 2605. This trigger voltage from the QT of was used to switch the applied voltage between the two EO pump reservoirs on the microchip device.

The ability to rapidly switch between analyte and reference solutions and obtain a stable response can be important for maintaining a high sampling duty cycle. In this device, the voltage applied at the EO pump channels generated both the EOF and the ESI potential. When the voltage was turned off, the fluid flow stopped immediately preventing droplet formation on the electrospray tip and minimizing the time required for the electrospray to be restarted. Although electrospray could be generated from both emitters simultaneously, signal was only observed from one emitter at a time despite attempts to optimize emitter positions and applied voltages. The Coulombic repulsion between electrospray plumes likely prevented simultaneous detection. It may be possible to achieve simultaneous detection by reorientation of the ESI emitters, the design of alternative inlets such as an ion funnel, or the use of multiple mass spectrometer inlets. However, sequential introduction of the analyte and reference materials may be preferable for reasons discussed above.

A single integrated electrospray emitter was characterized and found that the sensitivity and stability were comparable to a commercial capillary nanospray emitter such as that described in Mellors, J. S.; Qorbounov, V.; Ramsey, R. S.; Ramsey, J. M. Fully integrated glass microfluidic device for performing high-efficiency capillary electrophoresis and electrospray ionization mass spectrometry. *Anal. Chem.*

2008, 80, 6881. The sensitivity of a single emitter in isolation was compared to a single emitter in the sequentially operated, dual ESI configuration. For the single emitter in isolation configuration, the analyte emitter was aligned on axis with the mass spectrometer inlet orifice and the reference emitter was floated (i.e., no electrical contact was made to any channels connected to the reference emitter). For the sequentially operated, dual emitter configuration, both emitters were positioned an equal distance from the axis of the mass spectrometer inlet orifice and 0 kV was applied to the EO pump B channel. In both configurations, the voltage applied to the EO pump A channel was optimized for the highest signal from the analyte emitter. An infusion of leucine enkephalin revealed a similar composition of ions for both configurations; however, a 12% decrease in signal intensity was observed for the sequentially operated, dual emitter configuration.

Figure 16A:
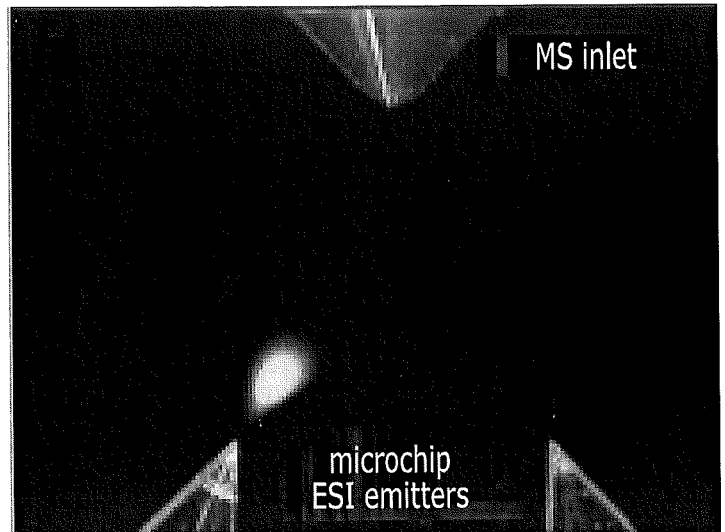
FIGS. 16A and 16B are digital photographs of the microchip with electrospray plumes from the different ESI nozzles (in FIG. 16A, the first emitter is active, and in FIG. 16B, the second emitter is active) projecting toward the MS (mass spectrometer) inlet with the plumes illuminated by (green) diode lasers according to embodiments of the present invention.
Figure 16B:
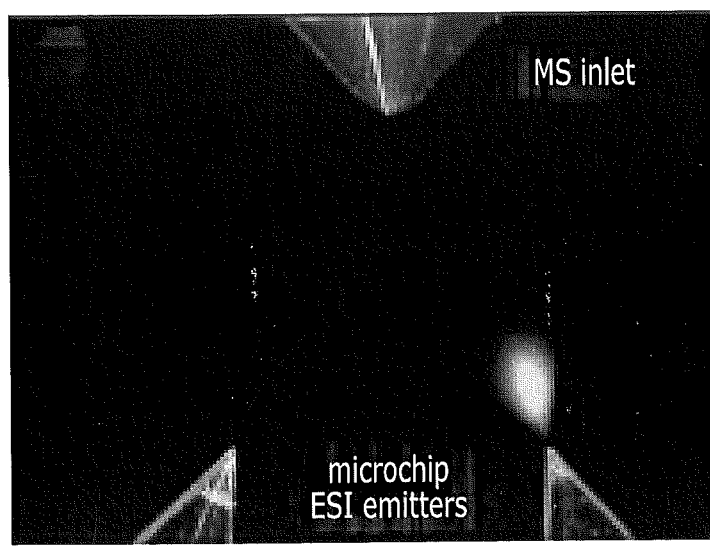

To demonstrate the speed at which two solutions can be analyzed, leucine enkephalin (analyte emitter) and reserpine (reference emitter) were sequentially electrosprayed at 2 s intervals. Photographs of the laser light scatter from the electrospray plumes are shown in FIG. 16. Reconstructed ion chromatograms for the [M+H]+ ions of leucine enkephalin (556.2771 m/z) and reserpine (609.2812 m/z), as measured by the T of instrument, are shown in FIGS. 17A and 17B). Each time the voltage was applied, the electrospray signal immediately recovered from the "off" state to its previous signal intensity. In this experiment, the ion intensities of the analyte and reference signals were approximately equal. A reconstructed ion chromatogram for both ions, shown in FIG. 17C, had a relative standard deviation of 7.2%. Even with the fast data acquisition rate (~15 Hz), large spikes or dips in the combined signal were not observed which demonstrate a seamless transition from one electrospray source to another. A portion of the time scale in FIG. 17 is expanded in FIG. 18 to reveal the switching speed between electrospray signals. At the time of 14.52 s the reference electrospray was turned off and the analyte electrospray was turned on. Although there were not enough data points to accurately determine the switching time, this data shows that the switch occurred in less than 70 ms (the time required for 1 summed scan and 2 interscan delays). Video imaging of the light scattered by the electrospray plume suggests that the switching time was less than 33 ms.

Figure 19A:
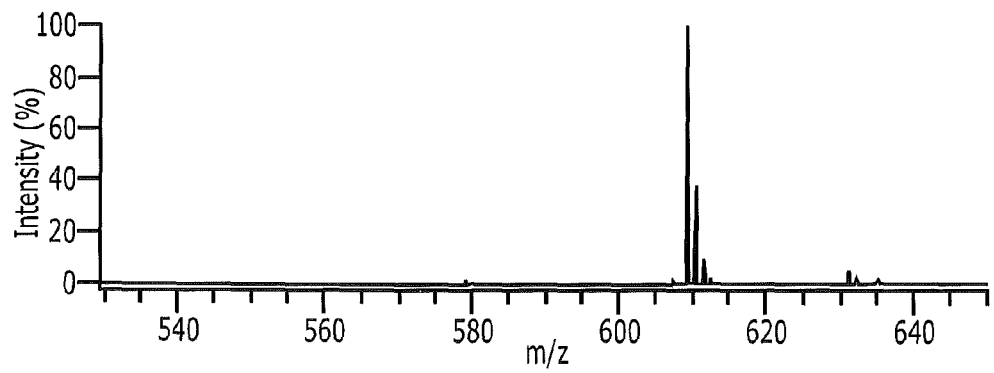
FIGS. 19A and 19B are graphs of intensity (percentage versus m/z of about 1 minute of summed mass spectra.
Figure 19B:
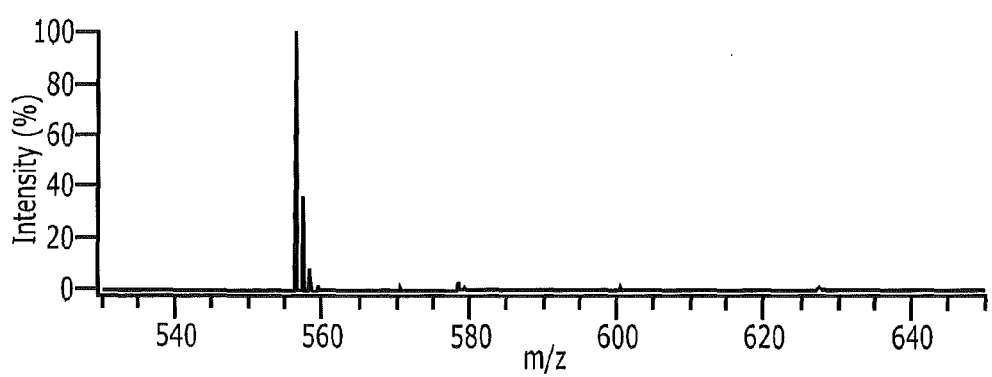
Figure 20:
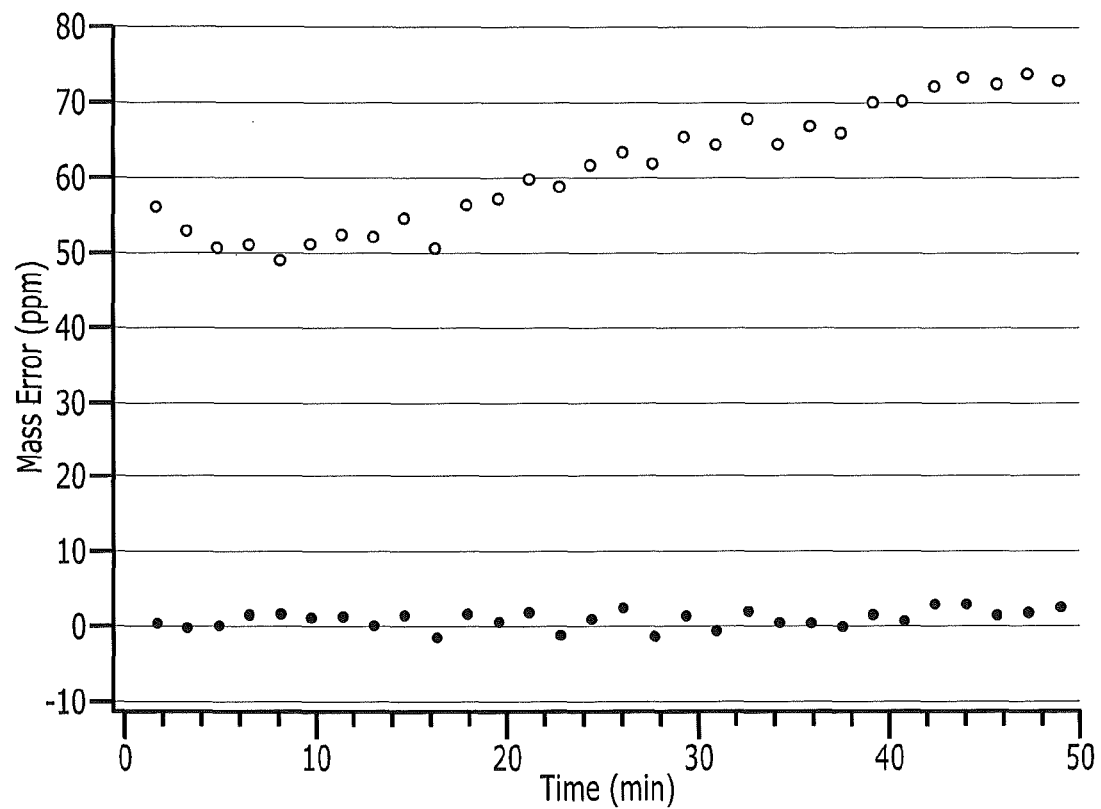
FIG. 20 is a graph of mass error (ppm) versus time (min) for mass measurement errors for infusion ESI-MS of leucine enkephalin according to embodiments of the present invention. The open circles are raw data and the solid closed circles are for corrected data.

The microchip dual ESI device was synchronized with the QT of mass spectrometer and used for infusion ESI-MS with internal calibration. During these experiments 1 reference scan was completed every 5 s. The software (MassLynx, Waters Corp.) automatically stored the reference and analyte data in separate data files. Ideally there should be no analyte signal present in the reference data file and no reference signal in the analyte data file. To quantify the amount of crosstalk, 1 min of data from the reference and analyte data file was summed and is shown in FIG. 19. No analyte signal was found in the reference data file and vice versa. The raw analyte data was stored and the "accurate mass measure" function in the software (MassLynx, Waters Corp.) was later used to apply a "continuous masslock correction" using the reserpine [M+H]+ ion. A comparison of the mass error between the raw and corrected analyte signal is shown in FIG. 20. Each data point represents 12 spectra from the analyte signal (leucine enkephalin, [M+H]+) that were summed, smoothed (twice by Savitzky-Golay, 4 channels) and centroided (top 80% of peak). The mass error root mean square values for the raw and corrected analyte signal were 61.9 ppm and 1.4 ppm, respectively. All corrected measurements had a mass error less than 3 ppm, which is within the 5 ppm specification for the commercial dual ESI source on this instrument.

A simple microfluidic device was used for sequential electrospray of analyte and reference solutions without the need for external pressure sources or any moving parts. In this demonstration, a single ion was used for internal calibration; however, multiple ions over the entire m/z range of interest may also be used to improve the mass accuracy. In addition to internal calibration, the dual emitter device may prove useful for monitoring multiple microfluidic separations with a single mass spectrometer.

The system of claim 1 or 3 or the method claims, claim 11-13, or the microchip claim 22 et seq., in the claim set that follows can be configured so that the first ESI emitter is an analyte spray emitter and the second ESI emitter is a reference spray emitter. The system and methods can be configured to adjust analyte data associated with the ESI analyte emitter collected by the mass spectrometer using reference data associated with the ESI reference emitter collected by the mass spectrometer to provide corrected analyte data measurements.

The method of claim 11 can include electronically adjusting analyte data using the reference data of at least one of the emitters and/or the acquiring data step can be carried out by obtaining reference data from at least one of the emitters before and/or after obtaining calibration data from at least one of the other emitters.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A mass spectrometer analyzer system, comprising:
a mass spectrometer with an inlet orifice; and
a flat microchip comprising a perimeter with four sides and at least a first and second monolithic ESI (electrospray ionization) emitter, wherein the first and second ESI emitters reside on one side of the microchip and, during operation, are aligned proximate the mass spectrometer inlet orifice; and
a control circuit configured to control fluid flow in the microchip to substantially synchronize respective ESI emitter spray with data acquisition of the mass spectrometer; and
at least one power supply in communication with the microchip, wherein the control circuit is in communication with the at least one power supply and is configured to direct the at least one power supply to deliver power to the microchip to controllably cause the at least first and second ESI emitters to spray,
wherein the at least first and second ESI emitters are in communication with a respective EO pump channel held by the microchip, and wherein the at least one power supply comprises a first power supply in communication with the first ESI emitter and a second power supply in communication with the second ESI emitter, and wherein the control circuit is configured to sequentially operate the first and second power supplies and synchronize the mass spectrometer data acquisition of emitter spray with switching of the first and second power supplies.

2. The system of claim 1, wherein the control circuit is configured to sequentially power the first and second ESI emitters.

3. The system of claim 1, wherein the mass spectrometer has an on-board mechanical baffle output circuit with a trigger voltage, and wherein the control circuit is configured to switch the first and second power supplies on and off using the trigger voltage.

4. The system of claim 1, wherein the microchip is rigid and has the first and second ESI emitters positioned proximate a single corner of the microchip.

5. The system of claim 1, wherein the microchip is rigid and has at least the first and second ESI emitters positioned spaced inwardly from corners and apart from each other, wherein the microchip also includes first and second fluid channels that converge on each other as they travel toward respective first and second ESI emitters so that virtual extensions of the first and second fluid channels intersect at a location that is a distance between 1 mm and 10 mm beyond a tip of the first and second ESI emitters.

6. The system of claim 1, wherein the ESI emitters are stacked ESI emitters that have sharp pointed tips.

7. The system of claim 1, wherein the microchip is rigid and the at least first and second ESI emitters are provided as a series of between about 2-100 closely spaced emitters residing on one corner of the microchip arranged and configured to spray fluid at an angle outward from the one corner.

8. A method of obtaining sample data, comprising:
providing a microchip with EO pump channels and between about 2-100 monolithic integrated separate ESI (electrospray ionization) emitters closely spaced apart about a single corner of the microchip, the ESI emitters having sharp tips, wherein the EO pump channels are curvilinear with a forwardmost segment residing proximate a respective ESI emitter tip;
activating at least one emitter by supplying voltage to a corresponding EO pump channel; and
acquiring signal data from spray plumes emitted by the respective separate ESI emitters using a mass spectrometer positioned proximate the microchip.

9. The method of claim 8, wherein the activating step is carried out by selectively activating one emitter or one emitter set at a time by supplying a high voltage to a corresponding EO pump channel.

10. The method of claim 9, further comprising electronically synchronizing the mass spectrometer data acquisition with the activating step.

11. The method of claim 10, wherein the electronically synchronizing step is carried out using an electrical component onboard the mass spectrometer.

12. The method of claim 9, wherein the integrated separate ESI emitters comprise stacked emitters.

13. The method of claim 9, wherein the ESI emitters are provided as a first set of emitters that concurrently spray plumes in response to the activating step and a second set of emitters that concurrently spray plumes in response to the activating step.

14. A method of obtaining sample data, comprising:
providing a microchip with EO pump channels and monolithic integrated separate at least first and second ESI emitters residing on a first end of the microchip;
activating at least one emitter by supplying voltage to a corresponding EO pump channel, wherein the activating step is carried out by selectively activating one emitter or one emitter set at a time by supplying a high voltage to a corresponding EO pump channel;
acquiring signal data from spray plumes emitted by the respective separate emitters using a mass spectrometer positioned proximate the microchip; and
electronically synchronizing the mass spectrometer data acquisition with the activating step, wherein the electronically synchronizing step is carried out using an electrical component onboard the mass spectrometer,
wherein the onboard component comprises a baffle control circuit having a trigger voltage output used to switch power supplies used to apply the voltage to the microchip EO pump channels.

15. A method of obtaining sample data, comprising:
providing a microchip with EO pump channels and monolithic integrated separate at least first and second ESI emitters residing on a first end of the microchip;
activating at least one emitter by supplying voltage to a corresponding EO pump channel, wherein the activating step is carried out by selectively activating one emitter or one emitter set at a time by supplying a high voltage to a corresponding EO pump channel; and
acquiring signal data from spray plumes emitted by the respective separate emitters using a mass spectrometer positioned proximate the microchip,
wherein the integrated separate ESI emitters comprise stacked emitters, and
wherein the stacked emitters reside closely spaced apart about a single corner of the microchip.

16. A method of obtaining sample data, comprising:
providing a microchip with EO pump channels and monolithic integrated separate at least first and second ESI emitters residing on a first end of the microchip;
activating at least one emitter by supplying voltage to a corresponding EO pump channel, wherein the activating step is carried out by selectively activating one emitter or one emitter set at a time by supplying a high voltage to a corresponding EO pump channel; and
acquiring signal data from spray plumes emitted by the respective separate emitters using a mass spectrometer positioned proximate the microchip,
wherein the emitters are between about 2-100 emitters closely spaced apart about a single corner of the microchip.

17. A microchip for use with a mass spectrometer, comprising:
a substantially rigid and planar microchip body;
at least first and second fluid channels formed into the microchip body; and
a plurality of flat closely spaced integrated ESI (electrospray ionization) emitters of between 2-100 defined by sharp tips, one or more of the ESI emitters in fluid communication with the first fluid channel and one or more of the ESI emitters in fluid communication with the second fluid channel, wherein at least one of the first and second fluid channels converges toward the other as the first and second fluid channels travel toward respective ESI emitters,
wherein the ESI emitters are a plurality of closely spaced sharp tips residing about one corner of the microchip arranged and configured to spray fluid at an angle outward from the one corner.

18. The microchip of claim 17, wherein the first and second fluid channels converge toward each other so that virtual extensions of the first and second fluid channels intersect at a location that is a distance between 1 mm and 10 mm beyond a tip of the respective ESI emitters.

19. The microchip of claim 17, further comprising EO (electroosmotic) pump channels for the ESI emitters.

20. The microchip of claim 17, wherein the ESI emitters are provided as between about 4-100 closely spaced emitters positioned on the corner of the microchip.

21. The microchip of claim 17, wherein at least two of the ESI emitters are stacked at a common position on the corner of the microchip body and are arranged and configured to spray fluid at an angle outward from the one corner.

22. A method of forming a microchip with ESI emitters for use with a mass spectrometer, comprising:
   providing a first substantially rigid substrate;
   forming fluid flow channels thereon;
   attaching a second substrate to the first substrate to enclose the fluid flow channels therebetween; then
   forming pointed spray tip projections on a first end of the attached first and second substrates to define between about 2-100 monolithic integrated separate ESI (electrospray ionization) emitters closely spaced apart about a single corner of the microchip.

23. The method of claim 22, wherein the forming projections step is carried out by cutting sharp tips into the first and second substrates.

24. The method of claim 22, further comprising forming EO (electroosmotic) pump channels and nanojunctions to connect a first fluid channel to a first EO pump channel and a second fluid channel to a second EO pump channel, the nanojunctions residing proximate a respective ESI emitter.

* * * * *

UNITED STATES PATENT AND TRADEMARK OFFICE
CERTIFICATE OF CORRECTION

PATENT NO. : 9,006,648 B2
APPLICATION NO. : 14/001549
DATED : April 14, 2015
INVENTOR(S) : Ramsey et al.

It is certified that error appears in the above-identified patent and that said Letters Patent is hereby corrected as shown below:

In the specification:
Column 12, Line 13: Please correct "1 mL/min to 1000 mL/min."
 to read -- 1 nL/min to 1000 nL/min. --

Column 14, Line 60: Please correct "stacked microchip 10,"
 to read -- stacked microchip 10$_s$ --

Column 17, Line 32: Please correct "BO pump" to read -- EO pump --

Column 20, Line 8: Please correct "QS/390" to read -- OS/390 --

Column 22, Line 13: Please correct "(QT of)" to read -- (QTof) --

Column 22, Line 14: Please correct "QT of" to read -- QTof --

Column 22, Line 15: Please correct "a T of mass" to read -- a Tof mass --

Column 22, Lines 17 and 18: Please correct "QT of" to read -- QTof --

Column 22, Line 19: Please correct "the T of" to read -- the Tof --

Column 22, Line 24: Please correct "the QT of" to read -- the QTof --

Column 22, Line 40: Please correct "the QT of" to read -- the QTof --

Signed and Sealed this
Twenty-second Day of December, 2015

Michelle K. Lee
*Director of the United States Patent and Trademark Office*